(12) United States Patent
Maruyama et al.

(10) Patent No.: US 9,856,237 B2
(45) Date of Patent: Jan. 2, 2018

(54) PYRAZINE DERIVATIVES

(71) Applicant: TEIJIN PHARMA LIMITED, Tokyo (JP)

(72) Inventors: Akinobu Maruyama, Tokyo (JP);
Susumu Takeuchi, Tokyo (JP);
Yoshimasa Takahashi, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 0 days.

(21) Appl. No.: 15/310,337

(22) PCT Filed: May 12, 2015

(86) PCT No.: PCT/JP2015/063654
§ 371 (c)(1),
(2) Date: Nov. 10, 2016

(87) PCT Pub. No.: WO2015/174417
PCT Pub. Date: Nov. 19, 2015

(65) Prior Publication Data
US 2017/0152242 A1    Jun. 1, 2017

(30) Foreign Application Priority Data
May 13, 2014  (JP) ................ 2014-099677

(51) Int. Cl.
*C07D 403/04*  (2006.01)
*C07D 403/14*  (2006.01)
*C07D 401/14*  (2006.01)
*C07D 409/14*  (2006.01)

(52) U.S. Cl.
CPC ......... *C07D 403/04* (2013.01); *C07D 401/14* (2013.01); *C07D 403/14* (2013.01); *C07D 409/14* (2013.01)

(58) Field of Classification Search
CPC .. C07D 241/12; C07D 241/16; C07D 241/18; C07D 241/24
See application file for complete search history.

(56) References Cited

U.S. PATENT DOCUMENTS

| 8,541,589 B2 | 9/2013 | Ouk et al. |
| 2010/0227864 A1 | 9/2010 | Shimizu et al. |
| 2012/0289506 A1 | 11/2012 | Shimizu et al. |
| 2013/0202573 A1 | 8/2013 | Ouk et al. |
| 2013/0281469 A1 | 10/2013 | Ouk et al. |

FOREIGN PATENT DOCUMENTS

| JP | 2006-36792 A | | 2/2006 | |
| JP | 2007-145786 A | | 6/2007 | |
| JP | 2013-528655 A | | 7/2013 | |
| WO | WO 2004/060870 | * | 7/2004 | ........... C07D 207/34 |
| WO | 2008/126899 A1 | | 10/2008 | |
| WO | 2014/077285 A1 | | 5/2014 | |

OTHER PUBLICATIONS

West, Anthony R., Solid State Chemistry and Its Applications, Wiley, New York, 1988, 358.*
International Search Report of PCT/JP2015/063654, dated Aug. 11, 2015. [PCT/ISA/210].

* cited by examiner

*Primary Examiner* — Erich A Leeser
(74) *Attorney, Agent, or Firm* — Sughrue Mion, PLLC

(57) ABSTRACT

Provided is a novel pyrazine derivative represented by the following formula (I) or a pharmaceutically acceptable salt thereof, or a solvate thereof which is useful for treating or preventing diseases in which URAT1 is involved, including gout, hyperuricemia, hypertension, renal diseases such as interstitial nephritis and the like, diabetes, arteriosclerosis, Lesch-Nyhan syndrome, and the like.

18 Claims, No Drawings

PYRAZINE DERIVATIVES

CROSS REFERENCE TO RELATED APPLICATIONS

This application is a National Stage of International Application No. PCT/JP2015/063654 filed May 12, 2015, claiming priority based on Japanese Patent Application No. 2014-099677, filed May 13, 2014, the contents of all of which are incorporated herein by reference in their entirety.

TECHNICAL FIELD

The present invention relates to a pyrazine derivative which is useful as a pharmaceutical. More specifically, the present invention relates to a pyrazine derivative and a pharmaceutically acceptable salt thereof, and a solvate thereof, which has URAT1 inhibitory activity and is useful for treating or preventing diseases in which URAT1 is involved, the diseases including gout, hyperuricemia, hypertension, kidney diseases such as interstitial nephritis and the like, diabetes, arteriosclerosis, Lesch-Nyhan syndrome, and the like.

BACKGROUND ART

Uric acid is the final product resulting from purine degradation in the liver. The primary route through which uric acid in the body is excreted is the kidney, and about two-thirds of it is excreted in the urine, with the remainder excreted in the stool. Blood uric acid levels are maintained in healthy individuals, but, when an excessive production of uric acid or a decreased excretion of uric acid occurs, this causes hyperuricemia.

Hyperuricemia, in which blood uric acid levels become elevated, is a factor that causes gout and urinary calculus, and furthermore it is said to contribute to nephropathy and arteriosclerosis. In addition, there have recently been an increasing number of reports that the higher the blood uric acid level, the higher the incidence rates of lifestyle-related diseases such as metabolic syndrome and hypertension, chronic kidney disease, and the like, and hyperuricemia is being recognized to be a risk factor for these diseases. Thus, an improvement in hyperuricemia is expected to lead to improvements in various diseases (Non-Patent Document 1).

Recently, the gene (SLC22A12) encoding a human renal urate transporter has been identified. The transporter (urate transporter 1, URAT1) encoded by this gene is a twelve-span transmembrane molecule belonging to the OAT family. Its mRNA is specifically expressed in the kidney, and further, its localization on the apical side of the proximal tubule has been observed in human kidney tissue sections. URAT1-mediated uric acid uptake has been shown by experiments using the *Xenopus* oocyte expression system. Furthermore, it has been reported that probenecid or benzbromarone, which inhibits URAT1, is useful as a therapeutic or prophylactic agent for hyperuricemia, gout, and the like (Non-Patent Document 2).

RELATED ART DOCUMENTS

Non-Patent Documents

[Non-Patent Document 1] The Guideline Revising Committee of Japanese Society of Gout and Nucleic Acid Metabolism, ed., *Guideline for the management of hyperuricemia and gout*, second edition, Medical Review (2010).

[Non-Patent Document 1] Enomoto A. et al., Nature 417, 447-452 (2002).

SUMMARY OF THE INVENTION

Problems to be Solved by the Invention

It is an object of the present invention to provide a novel compound having URAT1-inhibitory activity.

Additionally, it is another object of the present invention to provide a therapeutic or prophylactic agent for a URAT1-associated disease, such as gout, hyperuricemia, hypertension, renal disease such as interstitial nephritis, diabetes, arteriosclerosis, or Lesch-Nyhan syndrome, containing the novel compound having URAT1-inhibitory activity as an active ingredient.

Further, it is another object of the present invention to provide URAT1 inhibitor or pharmaceutical composition having inhibitory activity against URAT1.

Means of Solving the Problems

The present inventors conducted diligent research in order to solve the above problems and, as a result, reached the following invention. That is, the present invention is a pyrazine derivative represented by the following formula (I) or a pharmaceutically acceptable salt thereof, or a solvate thereof. Furthermore, the pyrazine derivative and the pharmaceutically acceptable salt thereof, and the solvate thereof of the present invention have excellent URAT1 inhibitory activity.

[Chemical formula 1]

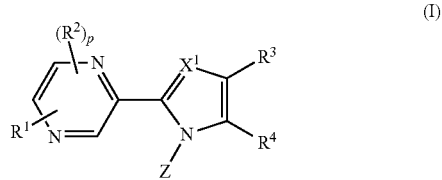

(I)

wherein, $X^1$ represents a nitrogen atom or CH; $R^1$ represents a hydrogen atom, a $C_1$-$C_6$ alkyl group, a $C_3$-$C_6$ cycloalkyl group, a $C_2$-$C_6$ alkenyl group, a $C_2$-$C_6$ alkynyl group, a halogen atom, a trifluoromethyl group, a difluoromethyl group, a cyano group, a $C_2$-$C_7$ alkylcarbonyl group, a $C_1$-$C_6$ alkylsulfonyl group, a nitro group, an amino group, a di($C_1$-$C_6$ alkyl)amino group, a formyl group, a hydroxyl group, a $C_1$-$C_6$ alkoxy group, a $C_1$-$C_6$ alkylthio group, or a phenyl or phenoxy group optionally substituted with 1 to 3 $R^a$'s; $R^a$ represents a halogen atom, a $C_1$-$C_6$ alkyl group, a $C_3$-$C_6$ cycloalkyl group, or a $C_1$-$C_6$ alkoxy group; $R^2$ represents a $C_1$-$C_6$ alkyl group, a $C_3$-$C_6$ cycloalkyl group, or a $C_1$-$C_6$ alkoxy group; p represents any integer of 0 to 2; $R^3$ represents a hydrogen atom, a $C_1$-$C_6$ alkyl group, a $C_3$-$C_6$ cycloalkyl group, a $C_2$-$C_6$ alkenyl group, a $C_2$-$C_6$ alkynyl group, a $C_1$-$C_5$ alkoxy group, a $C_2$-$C_7$ alkylcarbonyl group, a $C_1$-$C_6$ alkylthio group, a halogen atom, a trifluoromethyl group, a difluoromethyl group, a cyano group, a phenyl group, a pyridyl group, a phenoxy group, or a COOR$^b$; $R^4$ represents a tetrazolyl group, —COOR$^c$, —CONHSO$_2$—($C_1$-$C_6$ alkyl), or any one of the following groups:

[Chemical formula 2]

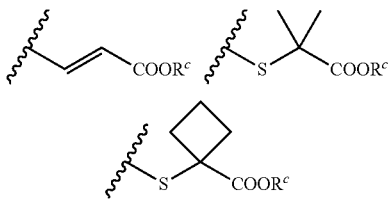

$R^b$ and $R^c$ may be the same or different and represent a hydrogen atom, or a $C_1$-$C_6$ alkyl group; Z represents any one of the following groups represented by Z1 to Z7:

[Chemical formula 3]

Z1
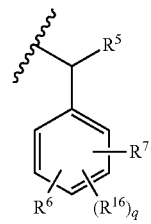

Z2
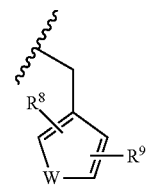

Z3
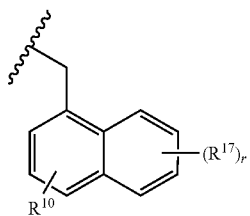

Z4
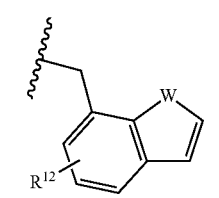

Z5

Z6
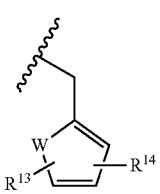

Z7

$R^5$ represents a hydrogen atom or a $C_1$-$C_6$ alkyl group; $R^6$ and $R^7$ may be the same or different and represent a hydrogen atom, a halogen atom, a $C_1$-$C_6$ alkyl group, a $C_1$-$C_5$ alkoxy group, a trifluoromethyl group, a trifluoromethoxy group, a cyano group, a nitro group, or a phenoxy group, or $R^6$ and $R^7$ together form a $C_1$-$C_3$ alkylenedioxy group; $R^8$, $R^9$, $R^{10}$, $R^{11}$, $R^{12}$, $R^{13}$, $R^{14}$, and $R^{15}$ each independently represent a hydrogen atom, a halogen atom, a $C_1$-$C_6$ alkyl group, a $C_1$-$C_6$ alkoxy group, a difluoromethyl group, a trifluoromethyl group, a cyano group, or a di($C_1$-$C_6$ alkyl)amino group; $R^{16}$ and $R^{17}$ may be the same or different and represent a halogen atom; q and r independently represent 0 or 1; W represents a sulfur atom, an oxygen atom, or $NR^d$; and $R^d$ represents a hydrogen atom, a $C_1$-$C_6$ alkyl group, or a benzyl group.

Furthermore, the present invention is a pharmaceutical composition comprising a pyrazine derivative represented by the above formula (I) or a pharmaceutically acceptable salt thereof, or a solvate thereof, and a pharmaceutically acceptable carrier; a URAT1 inhibitor containing the pyrazine derivative represented by the above formula (I) or a pharmaceutically acceptable salt thereof, or a solvate thereof as an active ingredient; and a preventive agent or a therapeutic agent for diseases in which URAT1 is involved such as gout, hyperuricemia, hypertension, kidney disease, diabetes, arteriosclerosis, Lesch-Nyhan syndrome, and the like, wherein the preventive agent or the therapeutic agent contains the pyrazine derivative represented by the above formula (I) or the pharmaceutically acceptable salt thereof, or the solvate thereof as an active ingredient.

Effects of the Invention

According to the present invention, there is provided a novel pyrazine derivative or a pharmaceutically acceptable salt thereof, or a solvate thereof, useful as a therapeutic or prophylactic agent for a URAT1-associated disease, such as gout, hyperuricemia, hypertension, renal disease such as interstitial nephritis, diabetes, arteriosclerosis, or Lesch-Nyhan syndrome.

MODE FOR CARRYING OUT THE INVENTION

In the following, there will be explained terms used singly or in combination in the present description. Unless otherwise noted, explanation of each substituent is common to all positions. Further, a combination of substituents and variables is allowed only when such a combination produces a chemically stable compound. When a substituent itself is substituted with two or more groups, these many groups can exist on the same carbon or on different carbons as long as a stable structure is generated.

In the present invention, the "halogen atom" means a fluorine atom, a chlorine atom, a bromine atom, and an iodine atom.

In the present invention, the "$C_1$-$C_6$ alkyl group" means a linear or branched aliphatic saturated hydrocarbon group of 1 to 6 carbon atoms, and a specific group includes, for example, a methyl group, an ethyl group, a propyl group, an isopropyl group, a butyl group, an isobutyl group, a tert-butyl group, a pentyl group, an isopentyl group, and a hexyl group.

In the present invention, the "$C_2$-$C_6$ alkenyl group" means a linear or branched aliphatic hydrocarbon group of 2 to 6 carbon atoms having an unsaturated double bond, and includes, for example, a vinyl group, a 1-propenyl group, a 2-propenyl group, a 2-methyl-1-propenyl group, a 2-methyl-2-propenyl group, a 2-buten-1-yl group, a 3-buten-1-yl group, a 2-penten-1-yl group, a 3-penten-1-yl group, a 4-penten-1-yl group, a 5-hexen-1-yl group, a 4-hexen-1-yl group, a 3-hexen-1-yl group, a 2-hexen-1-yl group, a 3-methyl-2-buten-1-yl group, a 3-methyl-3-penten-1-yl group, a 3-methyl-2-penten-1-yl group, a 4-methyl-3-penten-1-yl group, a 4-methyl-2-penten-1-yl group, a 2-methyl-2-penten-1-yl group, and the like.

In the present invention, the "$C_2$-$C_6$ alkynyl group" means a linear or branched aliphatic hydrocarbon group of 2 to 6 carbon atoms having an unsaturated triple bond, and includes, for example, an ethynyl group, a 1-propyn-1-yl group, a 2-propyn-1-yl group, a 2-butyn-1-yl group, a 3-butyn-1-yl group, a 2-pentyn-1-yl group, a 3-pentyn-1-yl group, a 4-pentyn-1-yl group, a 5-hexyn-1-yl group, a 4-hexyn-1-yl group, a 3-hexyn-1-yl group, a 2-hexyn-1-yl group, and the like.

In the present invention, the "$C_3$-$C_6$ cycloalkyl group" means a cyclic aliphatic hydrocarbon group of 3 to 6 carbon atoms, and a specific group includes, for example, a cyclopropyl group, a cyclobutyl group, a cyclopentyl group, and a cyclohexyl group.

In the present invention, the "$C_1$-$C_6$ alkoxy group" means a linear or branched aliphatic hydrocarbon-oxy group of 1 to 6 carbon atoms, and a specific group includes, for example, a methoxy group, an ethoxy group, a propoxy group, an isopropoxy group, a butoxy group, an isobutoxy group, a pentyloxy group, an isopentyloxy group, and a hexyloxy group.

In the present invention, the "$C_2$ to $C_7$ alkylcarbonyl group" means a group formed of a "$C_1$-$C_6$ alkyl group" and a carbonyl group and includes, for example, an acetyl group, a propionyl group, a butyryl group, an isobutyryl group, a n-pentylcarbonyl group, a sec-butylcarbonyl group, a tert-butylcarbonyl group, an isopentylcarbonyl group, a 2-methylbutylcarbonyl group, a 3-methylbutylcarbonyl group, a 1-ethylpropylcarbonyl group, a 1,1-dimethylpropylcarbonyl group, a 1,2-dimethylpropylcarbonyl group, a neopentylcarbonyl group, a 4-methylpentylcarbonyl group, a 3-methylpentylcarbonyl group, a 2-methylpentylcarbonyl group, a 1-methylpentylcarbonyl group, a 3,3-dimethylbutylcarbonyl group, a 2,2-dimethylbutylcarbonyl group, a 1,1-dimethylbutylcarbonyl group, a 1,2-dimethylbutylcarbonyl group, a 1,3-dimethylbutylcarbonyl group, a 2,3-dimethylbutylcarbonyl group, a 1-ethylbutylcarbonyl group, a 2-ethylbutylcarbonyl group, a n-hexylcarbonyl group, and the like.

In the present invention, the "$C_1$-$C_6$ alkylsulfonyl group" means a group formed of a "$C_1$-$C_6$ alkyl group" and a sulfonyl group and includes, for example, a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group, a hexylsulfonyl group, and the like.

In the present invention, the "di ($C_1$-$C_6$ alkyl)amino group" means an amino group having the same or different two "$C_1$-$C_6$ alkyl groups" substituted on a nitrogen atom and includes, for example, a dimethylamino group, a diethylamino group, a dipropylamino group, a diisopropylamino group, a dibutylamino group, a diisobutylamino group, a di(sec-butyl)amino group, a di(tert-butyl)amino group, a dipentylamino group, a dihexylamino group, and the like.

In the present invention, the "$C_1$-$C_6$ alkylthio group" means a group formed of a "$C_1$-$C_6$ alkyl group" and a thio group and includes, for example, a methylthio group, an ethylthio group, a propylthio group, an isopropylthio group, a butylthio group, an isobutylthio group, a sec-butylthio group, a tert-butylthio group, a pentylthio group, a neopentylthio group, a tert-pentylthio group, a 2-methylbutylthio group, a hexylthio group, an isohexylthio group, and the like.

In the present invention, the "$C_1$-$C_3$ alkylenedioxy group" means a group formed of a $C_1$-$C_3$ alkylene and two oxy groups. For example, there may be mentioned a methylenedioxy (—OCH$_2$O—), ethylenedioxy (—OCH$_2$CH$_2$O—), trimethylenedioxy (—OCH$_2$CH$_2$CH$_2$O—), propyleneoxy (—OCH$_2$CH(CH$_3$)O—) group, and the like.

In the present invention, the "$C_1$-$C_3$ alkylene group" means a bivalent group formed by loss of two hydrogen atoms from the same carbon atom or different two carbon atoms of a saturated linear or branched aliphatic hydrocarbon having 1 to 3 carbon atoms, and includes for example, a methylene, ethylene, or trimethylene group, and the like.

In addition, among the above-mentioned definitions, the "C" in, for example, "$C_1$" represents a carbon atom and the number that follows indicates the number of the carbon atoms. For example, "$C_1$-$C_6$" indicates a range from 1 carbon atom to 6 carbon atoms.

The present invention relates to a compound represented by the formula (I) or a pharmaceutically acceptable salt thereof, or a solvate thereof.

[Chemical formula 4]

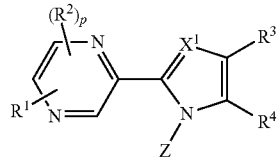

(I)

In the formula (I), $X^1$ represents a nitrogen atom or CH. Either case is preferable but the nitrogen atom is more preferable.

In the formula (I), $R^1$ represents a hydrogen atom, a $C_1$-$C_6$ alkyl group, a $C_3$-$C_6$ cycloalkyl group, a $C_2$-$C_6$ alkenyl group, a $C_2$-$C_6$ alkynyl group, a halogen atom, a trifluoromethyl group, a difluoromethyl group, a cyano group, a $C_2$-$C_7$ alkylcarbonyl group, a $C_1$-$C_6$ alkylsulfonyl group, a nitro group, an amino group, a di($C_1$-$C_6$ alkyl)amino group, a formyl group, a hydroxyl group, a $C_1$-$C_6$ alkoxy group, a $C_1$-$C_6$ alkylthio group, a phenyl group optionally substituted with 1 to 3 $R^a$'s, or a phenoxy group optionally substituted with 1 to 3 $R^a$'s.

$R^a$ represents a halogen atom, a $C_1$-$C_6$ alkyl group, a $C_3$-$C_6$ cycloalkyl group, or a $C_1$-$C_6$ alkoxy group.

As $R^1$, preferable is a hydrogen atom, a $C_1$-$C_6$ alkyl group, a $C_3$-$C_6$ cycloalkyl group, a halogen atom, a trifluoromethyl group, a cyano group, a hydroxyl group, a $C_1$-$C_6$ alkoxy group, a phenyl group, or a phenoxy group, and above all, more preferable is a hydrogen atom, a methyl group, an ethyl group, a cyclopropyl group, an isopropyl group, a methoxy group, an ethoxy group, a cyano group, a hydroxyl group, a phenyl group, or a phenoxy group.

Further, the position of substitution of $R^1$ is preferably a meta position as shown in the following formula (Ia).

[Chemical formula 5]

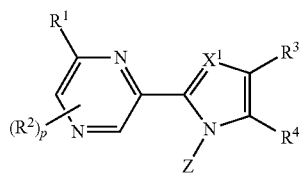

(Ia)

In the formula (I), $R^2$ represents a $C_1$-$C_6$ alkyl group, a $C_3$-$C_6$ cycloalkyl group, or a $C_1$-$C_6$ alkoxy group; and p represents an integer of 0 to 2.

As p, preferable is 0.

In the formula (I), $R^3$ represents a hydrogen atom, a $C_1$-$C_6$ alkyl group, a $C_3$-$C_6$ cycloalkyl group, a $C_2$-$C_6$ alkenyl group, a $C_2$-$C_6$ alkynyl group, a $C_1$-$C_6$ alkoxy group, a $C_2$-$C_7$ alkylcarbonyl group, a $C_1$-$C_6$ alkylthio group, a halogen atom, a trifluoromethyl group, a difluoromethyl group, a cyano group, a phenyl group, a pyridyl group, a phenoxy group, or $COOR^b$.

As $R^3$, preferable is a hydrogen atom, a $C_1$-$C_6$ alkyl group, or a halogen atom and, above all, more preferable is a hydrogen atom, a methyl group, or a chlorine atom.

In the formula (I), $R^4$ represents a tetrazolyl group, —$COOR^c$, —$CONHSO_2$—($C_1$-$C_6$ alkyl), or a group shown by any one of the following:

[Chemical formula 6]

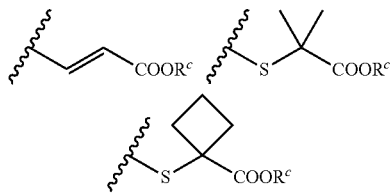

$R^b$ and $R^c$ may be the same or different and represent a hydrogen atom or a $C_1$-$C_6$ alkyl group.

As $R^4$, preferable is —$COOR^c$ and, above all, a carboxyl group is more preferable.

In the formula (I), Z represents any one of groups represented by the following formulas Z1 to Z7.

[Chemical formula 7]

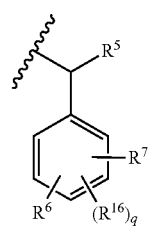

Z1

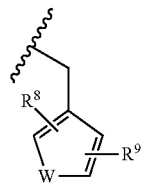

Z2

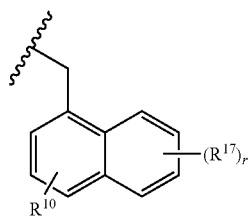

Z3

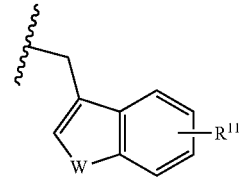

Z4

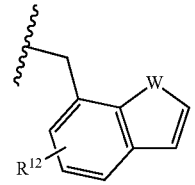

Z5

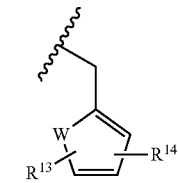

Z6

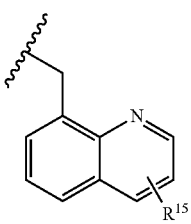

Z7

In Z1, $R^5$ represents a hydrogen atom or a $C_1$-$C_6$ alkyl group. $R^6$ and $R^7$ may be the same or different and represent a hydrogen atom, a halogen atom, a $C_1$-$C_6$ alkyl group, a $C_1$-$C_6$ alkoxy group, a trifluoromethyl group, a trifluoromethoxy group, a cyano group, a nitro group, or a phenoxy group, or $R^6$ and $R^7$ together form a $C_1$-$C_3$ alkylenedioxy group. $R^{16}$ represents a halogen atom; and q represents 0 or 1.

In Z2 to Z7, $R^8$, $R^9$, $R^{10}$, $R^{11}$, $R^{12}$, $R^{13}$, $R^{14}$, and $R^{15}$ represent each independently a hydrogen atom, a halogen atom, a $C_1$-$C_6$ alkyl group, a $C_1$-$C_6$ alkoxy group, a difluoromethyl group, a trifluoromethyl group, a cyano group, or a di($C_1$-$C_6$ alkyl)amino group; W represents a sulfur atom, an oxygen atom, or $NR^d$; $R^{17}$ may be the same or different and represents a halogen atom; r represents 0 or 1; and $R^d$ represents a hydrogen atom, a $C_1$-$C_6$ alkyl group, or a benzyl group.

As Z, preferable is Z1 or Z2 and, in that case, W is preferably a sulfur atom.

Above all, Z is preferably the following formula Z1a or Z2a.

[Chemical formula 8]

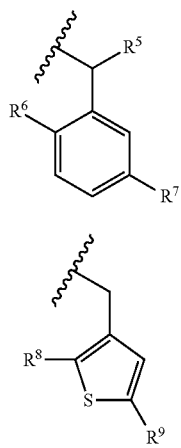

Z1a

Z2a

As $R^5$, preferable is a hydrogen atom. $R^6$, $R^7$, $R^8$, and $R^9$ each independently preferably represent a hydrogen atom, a halogen atom, or a $C_1$-$C_6$ alkyl group and, more preferably, a hydrogen atom, a chlorine atom, or a methyl group. In the case of Z1a, it is more preferable that $R^5$ represents a hydrogen atom, and $R^6$ and $R^7$ both represent chlorine atoms. In the case of Z2a, it is more preferable that $R^8$ and $R^9$ both represent chlorine atoms.

In Z3, a position of substitution of $R^{10}$ on a naphthalene ring is preferably 2-position, 4-position, or 8-position, and $R^{10}$ is preferably a hydrogen atom, a fluorine atom, a chlorine atom, a bromine atom, a methyl group, a methoxy group, a trifluoromethyl group, or a cyano group. Above all, preferable is a 2-methyl group, a 4-methyl group, a 8-methyl group, a 4-bromo group, a 8-methyl group, or a 8-bromo group. And r is preferably 0.

In Z4, W is preferably a sulfur atom. A position of substitution of $R^{11}$ on a benzothiophene, benzofuran, or indole ring is preferably 4-position or 5-position, and $R^{11}$ is preferably a hydrogen atom, a fluorine atom, a chlorine atom, a bromine atom, a methyl group, a methoxy group, a trifluoromethyl group, or a cyano group. Above all, preferable is a hydrogen atom, a 4-methyl group, a 4-chloro group, a 4-bromo group, a 4-trifluoromethyl group, a 5-methyl group, a 5-chloro group, or a 5-trifluoromethyl group.

In Z5, W is preferably a sulfur atom. A position of substitution of $R^{12}$ on a benzothiophene, benzofuran, or indole ring is preferably 5-position and $R^{12}$ is preferably a hydrogen atom or a fluoro group.

In Z6, W is preferably a sulfur atom. Positions of substitution of $R^{13}$ and $R^{14}$ on a thiophene, furan, or pyrrole ring are preferably 2- and 4-positions and they are preferably both chloro groups. In Z7, $R^{15}$ preferably represents a hydrogen atom.

In the formula (I), as a combination of $R^1$, $R^2$, $R^3$, $R^4$, p, Z ($R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, q, r, $R^d$), $R^a$, $R^b$, and $R^c$, preferable is a combination of the above-mentioned preferable groups and numbers, and more preferable is a combination of the more preferable groups and numbers.

Specific examples of the pyrazine derivative of the present invention, represented by the formula (I), include the following compounds.

TABLE 1

| Compound Number | Structure |
|---|---|
| A1 | 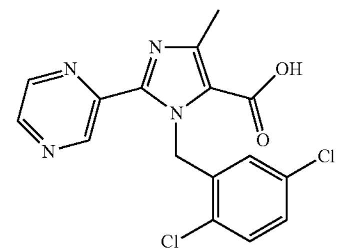 [SMILES: Cc1nc(-c2cnccn2)n(Cc2cc(Cl)ccc2Cl)c1C(=O)O] |
| A2 | 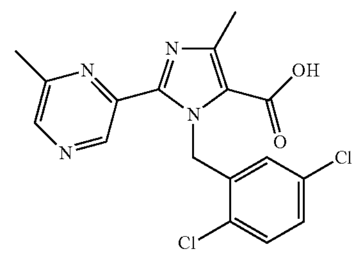 [SMILES: Cc1cncc(-c2nc(C)c(C(=O)O)n2Cc2cc(Cl)ccc2Cl)n1] |
| A3 | 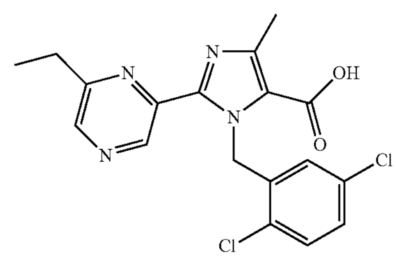 [SMILES: CCc1cncc(-c2nc(C)c(C(=O)O)n2Cc2cc(Cl)ccc2Cl)n1] |
| A4 | 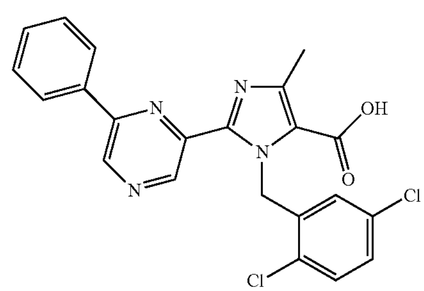 [SMILES: Cc1nc(-c2cncc(-c3ccccc3)n2)n(Cc2cc(Cl)ccc2Cl)c1C(=O)O] |
| A5 | 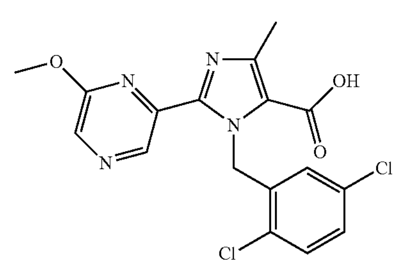 [SMILES: COc1cncc(-c2nc(C)c(C(=O)O)n2Cc2cc(Cl)ccc2Cl)n1] |

TABLE 1-continued
| Compound Number | Structure |
|---|---|
| A6 | 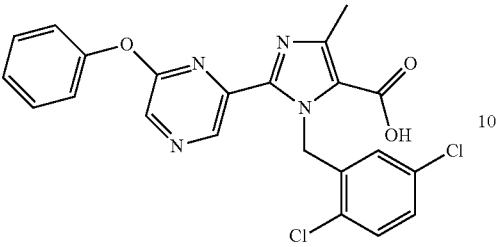 |
| A7 | 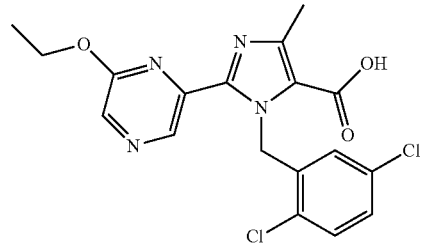 [SMILES: CCOc1cncc(-c2nc(C)c(C(=O)O)n2Cc2cc(Cl)ccc2Cl)n1] |
| A8 | 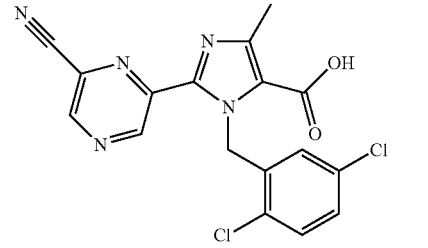 [SMILES: Cc1nc(-c2cncc(C#N)n2)n(Cc2cc(Cl)ccc2Cl)c1C(=O)O] |
| A9 | 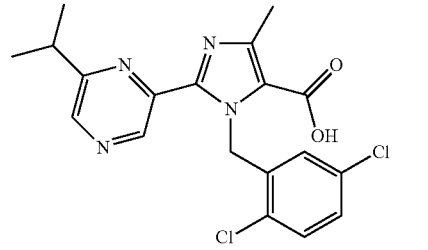 [SMILES: Cc1nc(-c2cncc(C(C)C)n2)n(Cc2cc(Cl)ccc2Cl)c1C(=O)O] |
| A10 | 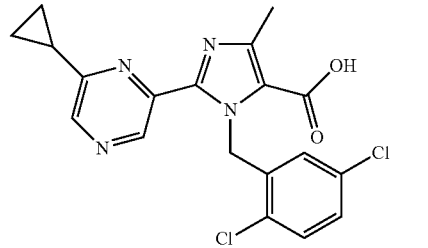 [SMILES: Cc1nc(-c2cncc(C3CC3)n2)n(Cc2cc(Cl)ccc2Cl)c1C(=O)O] |
| A11 | 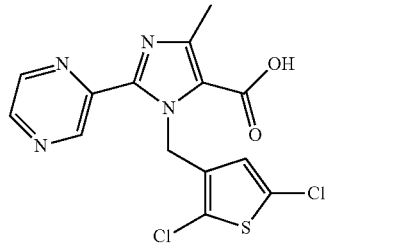 [SMILES: Cc1nc(-c2cnccn2)n(Cc2cc(Cl)sc2Cl)c1C(=O)O] |
| A12 | 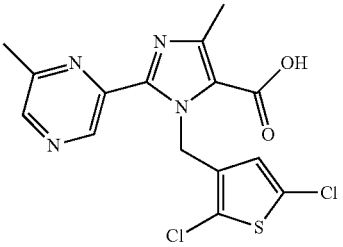 [SMILES: Cc1cncc(-c2nc(C)c(C(=O)O)n2Cc2cc(Cl)sc2Cl)n1] |
| A13 | 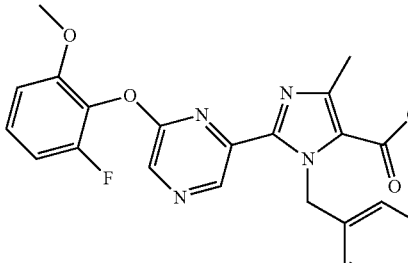 |
| A14 | 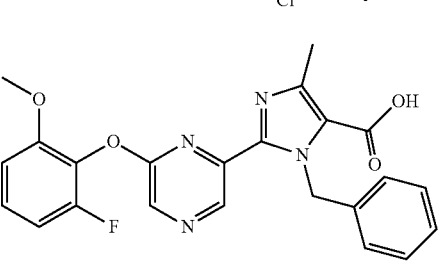 |
| A15 | 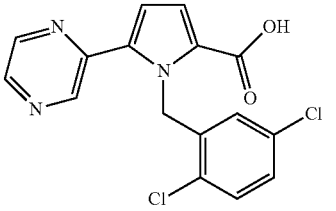 [SMILES: O=C(O)c1ccc(-c2cnccn2)n1Cc1cc(Cl)ccc1Cl] |
| A16 | 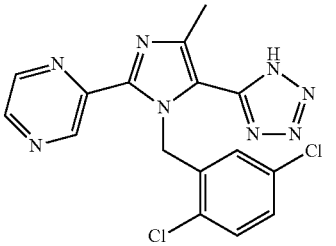 [SMILES: Cc1nc(-c2cnccn2)n(Cc2cc(Cl)ccc2Cl)c1-c1nnn[nH]1] |
| A17 | 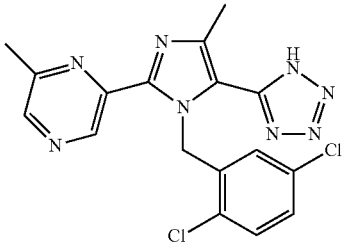 [SMILES: Cc1cncc(-c2nc(C)c(-c3nnn[nH]3)n2Cc2cc(Cl)ccc2Cl)n1] |

TABLE 1-continued
| Compound Number | Structure |
|---|---|
| A18 | 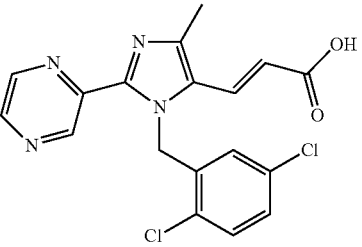 [SMILES: Cc1nc(-c2cnccn2)n(Cc2cc(Cl)ccc2Cl)c1/C=C/C(=O)O] |
| A19 | 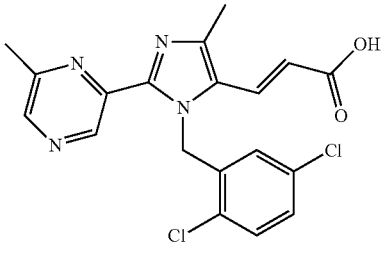 [SMILES: Cc1cncc(-c2nc(C)c(/C=C/C(=O)O)n2Cc2cc(Cl)ccc2Cl)n1] |
| A20 | 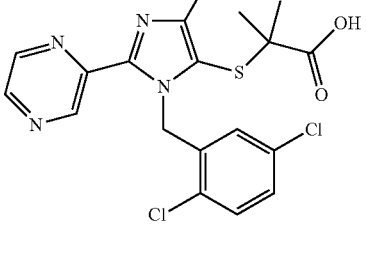 |
| A21 | 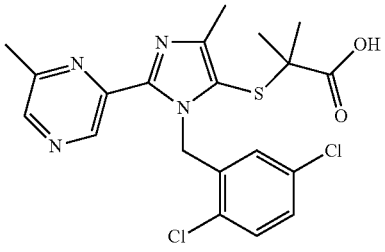 [SMILES: Cc1cncc(-c2nc(C)c(SC(C)(C)C(=O)O)n2Cc2cc(Cl)ccc2Cl)n1] |
| A22 | 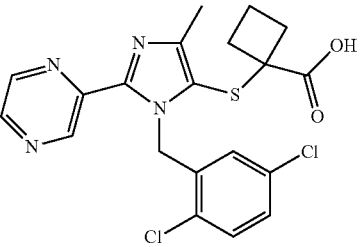 [SMILES: Cc1nc(-c2cnccn2)n(Cc2cc(Cl)ccc2Cl)c1SC1(C(=O)O)CCC1] |
| A23 | 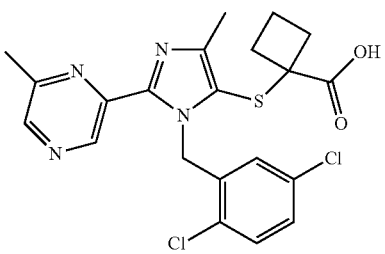 [SMILES: Cc1cncc(-c2nc(C)c(SC3(C(=O)O)CCC3)n2Cc2cc(Cl)ccc2Cl)n1] |
| A24 | 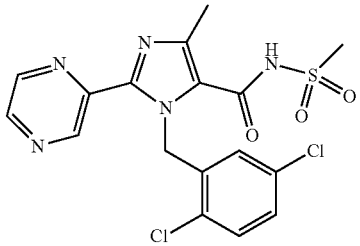 [SMILES: Cc1nc(-c2cnccn2)n(Cc2cc(Cl)ccc2Cl)c1C(=O)NS(C)(=O)=O] |
| A25 | 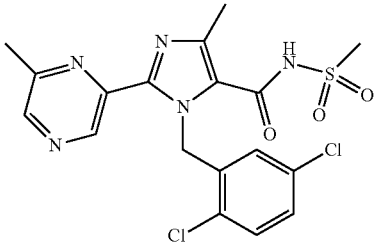 [SMILES: Cc1cncc(-c2nc(C)c(C(=O)NS(C)(=O)=O)n2Cc2cc(Cl)ccc2Cl)n1] |
| A26 | 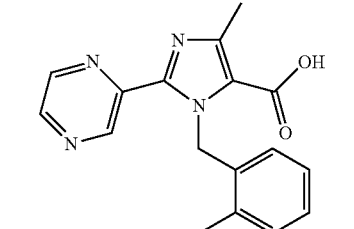 |
| A27 | 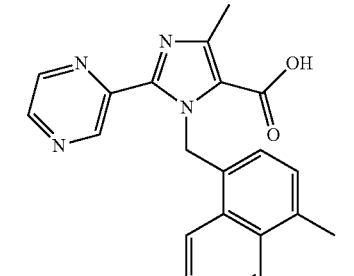 |
| A28 | 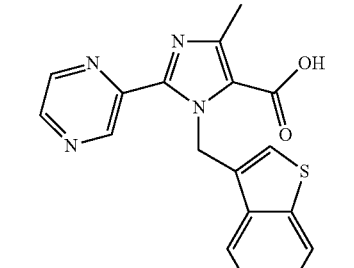 |

TABLE 1-continued

| Compound Number | Structure |
|---|---|
| A29 | 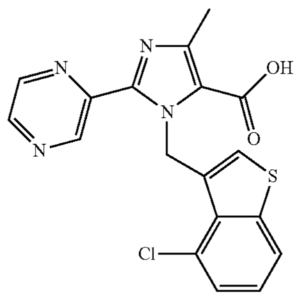 [SMILES: Cc1nc(-c2cnccn2)n(Cc2csc3cccc(Cl)c23)c1C(=O)O] |
| A30 | 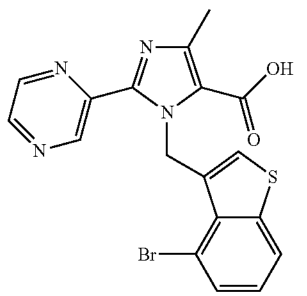 [SMILES: Cc1nc(-c2cnccn2)n(Cc2csc3cccc(Br)c23)c1C(=O)O] |
| A31 | 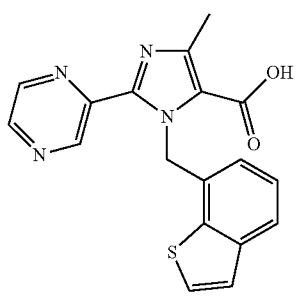 [SMILES: Cc1nc(-c2cnccn2)n(Cc2cccc3ccsc23)c1C(=O)O] |
| A32 | 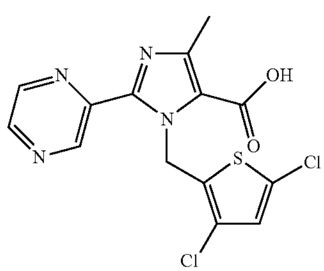 [SMILES: Cc1nc(-c2cnccn2)n(Cc2sc(Cl)cc2Cl)c1C(=O)O] |
| A33 | 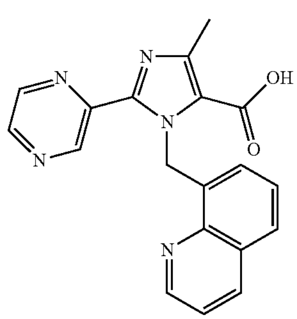 [SMILES: Cc1nc(-c2cnccn2)n(Cc2cccc3cccnc23)c1C(=O)O] |
| A34 | 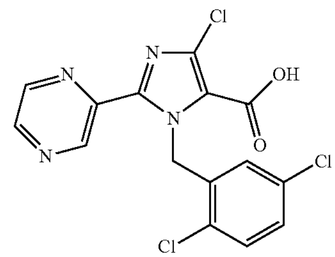 [SMILES: O=C(O)c1c(Cl)nc(-c2cnccn2)n1Cc1cc(Cl)ccc1Cl] |
| A35 | 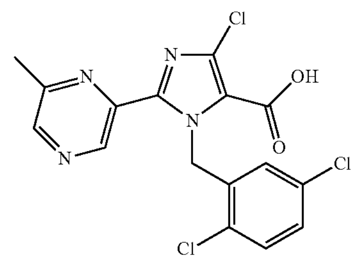 [SMILES: Cc1cncc(-c2nc(Cl)c(C(=O)O)n2Cc2cc(Cl)ccc2Cl)n1] |
| A36 | 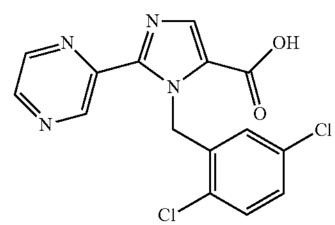 [SMILES: O=C(O)c1cnc(-c2cnccn2)n1Cc1cc(Cl)ccc1Cl] |
| A37 | 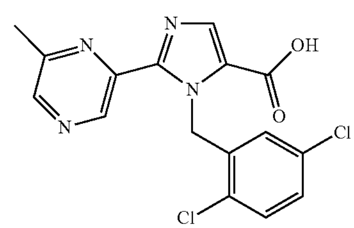 [SMILES: Cc1cncc(-c2ncc(C(=O)O)n2Cc2cc(Cl)ccc2Cl)n1] |
| A38 | 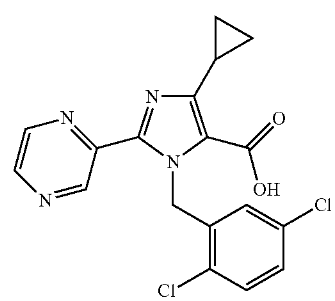 [SMILES: O=C(O)c1c(C2CC2)nc(-c2cnccn2)n1Cc1cc(Cl)ccc1Cl] |
| A39 | 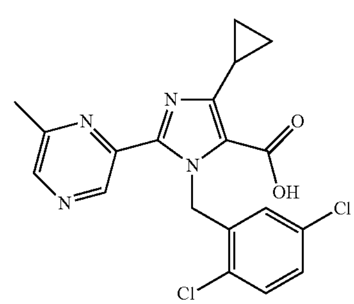 [SMILES: Cc1cncc(-c2nc(C3CC3)c(C(=O)O)n2Cc2cc(Cl)ccc2Cl)n1] |

Among these, preferable compounds are those shown in the following table.

TABLE 2

| Compound | Compound Name |
| --- | --- |
| A1 | 1-(2,5-dichlorobenzyl)-4-methyl-2-(pyrazin-2-yl)-1H-imidazole-5-carboxylic acid |
| A2 | 1-(2,5-dichlorobenzyl)-4-methyl-2-(6-methylpyrazin-2-yl)-1H-imidazole-5-carboxylic acid |
| A3 | 1-(2,5-dichlorobenzyl)-2-(6-ethylpyrazin-2-yl)-4-methyl-1H-imidazole-5-carboxylic acid |
| A4 | 1-(2,5-dichlorobenzyl)-4-methyl-2-(6-phenylpyrazin-2-yl)-1H-imidazole-5-carboxylic acid |
| A5 | 1-(2,5-dichlorobenzyl)-2-(6-methoxypyrazin-2-yl)-4-methyl-1H-imidazole-5-carboxylic acid |
| A6 | 1-(2,5-dichlorobenzyl)-4-methyl-2-(6-phenoxypyrazin-2-yl)-1H-imidazole-5-carboxylic acid |
| A7 | 1-(2,5-dichlorobenzyl)-2-(6-ethoxypyrazin-2-yl)-4-methyl-1H-imidazole-5-carboxylic acid |
| A8 | 2-(6-cyanopyrazin-2-yl)-1-(2,5-dichlorobenzyl)-4-methyl-1H-imidazole-5-carboxylic acid |
| A9 | 1-(2,5-dichlorobenzyl)-2-(6-isopropylpyrazin-2-yl)-4-methyl-1H-imidazole-5-carboxylic acid |
| A10 | 2-(6-cyclopropylpyrazin-2-yl)-1-(2,5-dichlorobenzyl)-4-methyl-1H-imidazole-5-carboxylic acid |
| A11 | 1-((2,5-dichlorothiophene-3-yl)methyl)-4-methyl-2-(pyrazin-2-yl)-1H-imidazole-5-carboxylic acid |
| A12 | 1-((2,5-dichlorothiophene-3-yl)methyl)-4-methyl-2-(6-methylpyrazin-2-yl)-1H-imidazole-5-carboxylic acid |
| A14 | 1-benzyl-2-(6-(2-fluoro-6-methoxyphenoxy)pyrazin-2-yl)-4-methyl-1H-imidazole-5-carboxylic acid |
| A15 | 1-(2,5-dichlorobenzyl)-2-(pyrazin-2-yl)-1H-pyrrole-5-carboxylic acid |

The present invention relates also to pharmaceutically acceptable salts of pyrazine derivatives represented by formula (I). Such salts include, for example, salts with inorganic acids, such as hydrochloric acid, hydrobromic acid, hydriodic acid, sulfuric acid, nitric acid, phosphoric acid, and carbonic acid; salts with organic acids, such as formic acid, acetic acid, propionic acid, trifluoroacetic acid, phthalic acid, oxalic acid, malonic acid, succinic acid, fumaric acid, maleic acid, lactic acid, malic acid, tartaric acid, citric acid, benzoic acid, methanesulfonic acid, ethanesulfonic acid, benzenesulfonic acid, and p-toluenesulfonic acid; salts with amino acids, such as lysine, arginine, ornithine, glutamic acid, and aspartic acid; salts with alkali metals, such as sodium, potassium, and lithium; salts with alkaline-earth metals, such as calcium and magnesium; salts with metals, such as aluminium, zinc, and iron; salts with organic bases, such as methylamine, ethylamine, diethylamine, trimethylamine, triethylamine, ethylenediamine, piperidine, piperazine, pyridine, picoline, ethanolamine, diethanolamine, triethanolamine, cyclohexylamine, dicyclohexylamine, N-methyl glucamine, and N,N'-dibenzylethylenediamine; ammonium salts, and the like.

The above-mentioned various pharmaceutically acceptable salts of the pyrazine derivative represented by the formula (I) can be suitably produced based on ordinary skill in the art.

The compound of the present invention includes stereoisomers, racemates, and every possible optically active substances of the pyrazine derivative represented by the formula (I). Further, the compound of the present invention sometimes generates tautomers depending on a combination of respective substituents, and these tautomers are also included in the compound of the present invention.

The present invention also relates to a solvate of the pyrazine derivative represented by the formula (I) or the pharmaceutically acceptable salt thereof. As such a solvent, there can be mentioned water, methanol, ethanol, 1-propanol, 2-propanol, butanol, tert-butanol, acetonitrile, acetone, methyl ethyl ketone, chloroform, ethyl acetate, diethyl ether, tert-butyl methyl ether, benzene, toluene, DMF, DMSO, and the like. Especially, there may be mentioned, as a preferable solvent, water, methanol, ethanol, 1-propanol, 2-propanol, acetonitrile, acetone, methyl ethyl ketone, and ethyl acetate.

<general synthetic example>

Synthesis of the pyrazine derivative represented by the formula (I) may be performed by any method but can be performed, for example, as shown in the following schemes A to D.

1) Scheme A

When $X^1$ is a nitrogen atom and $R^4$ is —COOR$^c$ or —CONHSO$_2$—(C$_1$-C$_6$ alkyl), a pyrazine derivative can be synthesized as shown in the following scheme A. That is, after a compound (A-2) is obtained by brominating a commercially available imidazole derivative (A-1), a compound (A-3) is obtained by N-alkylation of the compound (A-2) by a reaction using a base and a halide or by a Mitsunobu reaction using an alcohol. By a Stille coupling reaction using the compound (A-3) and a tin derivative, there is obtained a compound (A-4). If necessary, by hydrolyzing an ester group of the compound (A-4), there can be obtained a compound (A-5). Further, if necessary, by subjecting this material to a condensation reaction with an alkyl sulfonamide, there can be obtained an acyl sulfonamide entity (A-6).

Scheme A

[Chemical formula 9]

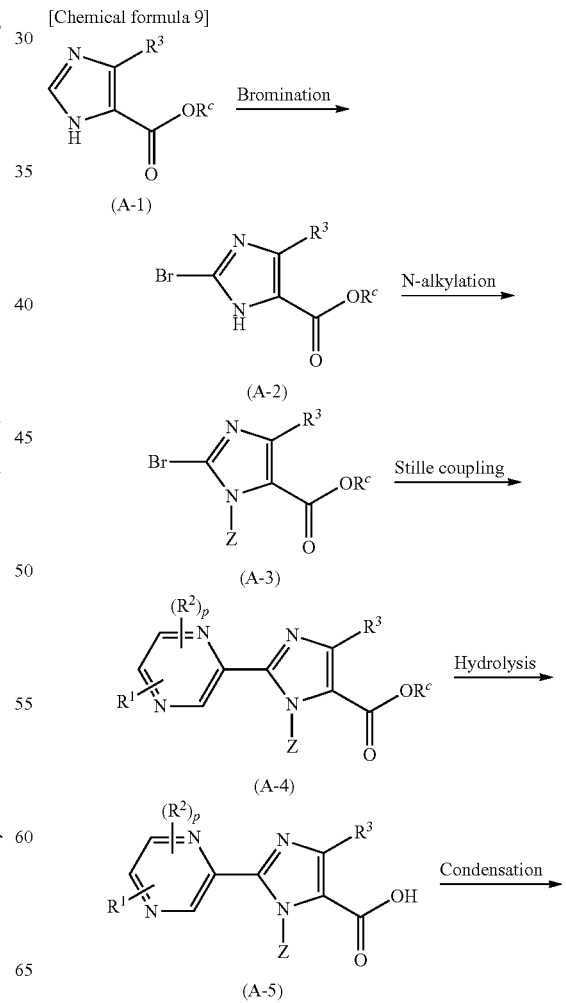

-continued

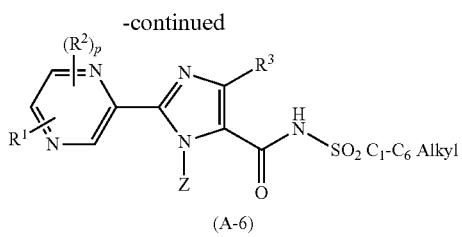

(A-6)

As a preferable reagent for bromination of the compound (A-1) to (A-2) in Scheme A, there can be mentioned bromine and N-bromosuccinimide (NBS). Furthermore, even though a solvent in this reaction is not particularly limited, there may be mentioned, for example, ethers such as tetrahydrofuran (THF), 1,4-dioxane, 1,2-dimethoxyethane, 1,2-diethoxyethane, and the like; acetonitrile; halogenated solvents such as dichloromethane, carbon tetrachloride, and the like; and mixed solvents of these. This reaction proceeds at temperatures from 0° C. to 100° C., but it is preferable to carry out the reaction at room temperature to 50° C.

With regard to N-alkylation of the compound (A-2) to (A-3), the compound (A-3) can be obtained by a reaction using a base and a halide, or by a Mitsunobu reaction using an alcohol. When a base and a halide are used, the base includes potassium carbonate, cesium carbonate, triethylamine, diisopropylethylamine, and sodium hydride. Among these, a preferable base includes potassium carbonate, cesium carbonate, triethylamine, and diisopropylethylamine. Further, the halide compound includes a chloride, a bromide, and an iodide, and a preferable halide includes a chloride and a bromide. A reaction temperature in the presence of a base and a halide is preferably from room temperature to 150° C., but more preferably, the reaction is conducted from 50° C. to 120° C. Furthermore, even though a solvent in this reaction is not particularly limited, there may be mentioned, for example, ethers such as tetrahydrofuran (THF), 1,4-dioxane, 1,2-dimethoxyethane, 1,2-diethoxyethane, and the like; amides such as dimethylformamide, N-methylpyrrolidone, and the like; toluene and xylene; and mixed solvents of these. Further, alkylation of the compound (A-2) to form the compound (A-3) proceeds also by the Mitsunobu reaction with an alcohol. As a condition of the Mitsunobu reaction, a phosphine compound, a condensing agent, an alcohol, and the compound (A-2) are mixed in an inert solvent to obtain the compound (A-3). The phosphine includes tributylphosphine, triphenylphosphine, tricyclohexylphosphine, and the like, but preferable is triphenylphosphine. Further, the condensing agent includes diethyl azodicarboxylate (DEAD) and diisopropyl azodicarboxylate (DIAD) as preferable condensing agents. The reaction temperature of this Mitsunobu reaction may be anywhere from 0° C. to 100° C., but the preferable reaction temperature is from room temperature to 80° C. In addition, even though a solvent in the Mitsunobu reaction is not particularly limited, there may be mentioned, for example, ethers such as tetrahydrofuran (THF), 1,4-dioxane, 1,2-dimethoxyethane, 1,2-diethoxyethane, and the like; amides such as dimethylformamide, N-methylpyrrolidone, and the like; halogenated solvents such as dichloromethane and the like; toluene and xylene; and mixed solvents of these.

The Stille coupling reaction of the compound (A-3) to form the compound (A-4) proceeds by heating the compound (A-3), a tin derivative, a palladium catalyst, and a base in a solvent which is inert to the reaction. This reaction is preferably carried out in an inert gas atmosphere. As the tin catalyst, a preferable example includes a trialkyltin derivative. Further, as the palladium catalyst, it is preferable to use [1,1'-bis(diphenylphosphino)ferrocene]dichloropalladium(II) ($PdCl_2(dppf)$), tetrakis(triphenylphosphine)palladium ($Pd(PPh_3)4$), and the like. Furthermore, as the base, a preferable base includes potassium carbonate and cesium carbonate. Further, even though a solvent in this reaction is not particularly limited, it is preferable to use, for example, ethers such as tetrahydrofuran (THF), 1,4-dioxane, 1,2-dimethoxyethane, 1,2-diethoxyethane, and the like; amides such as dimethylformamide, N-methylpyrrolidone, and the like; toluene and xylene; and mixed solvents of these. The reaction proceeds at a temperature from 50° C. to 150° C., but the reaction is carried out preferably from 80° C. to 120° C.

The hydrolysis reaction of the compound (A-4) to form the compound (A-5) proceeds by mixing the compound (A-4) with an equivalent or a little excess amount of a base in a mixed solvent including a solvent inert to the reaction and water. The hydrolysis is carried out usually for 1 to 24 hours. A preferable base includes sodium hydroxide, potassium hydroxide, and lithium hydroxide. In addition, even though the solvent is not particularly limited, it is preferable to carry out the reaction in a mixed solvent of an organic solvent and water, the organic solvent including, for example, tetrahydrofuran (THF), alcohols such as methanol, ethanol, and the like.

The condensation reaction of the compound (A-5) to form the compound (A-6) proceeds by mixing the compound (A-5) with an alkylsulfonamide in an inert solvent in the presence of a base and a condensing agent. The solvent includes, for example, ethers such as tetrahydrofuran (THF), 1,4-dioxane, 1,2-dimethoxyethane, 1,2-diethoxyethane, and the like; halogenated solvents such as dichloromethane, carbon tetrachloride, and the like; acetonitrile; and mixed solvents of these. A preferable solvent includes tetrahydrofuran (THF), dimethylformamide, and dichloromethane. The base includes potassium carbonate, cesium carbonate, triethylamine, diisopropylethylamine, sodium hydride, and the like, but a preferable base is triethylamine or diisopropylethylamine. The condensing agent includes dicyclohexylcarbodiimide (DCC), diphenylphosphoryl azide (DPPA), 1-ethyl-3-(3-dimethylaminopropyl)carbodiimide hydrochloride (EDCI or WSC), O-(7-azabenzotriazol-1-yl)-N,N,N',N'-tetramethyluronium hexafluorophosphate (HATU), O-(7-azabenzotriazol-1-yl)-N,N,N',N'-tetramethyluronium tetrafluoroborate (TATU), and the like, but preferable is WSC. The reaction temperature may be anywhere from 0° C. to 100° C., but the preferable reaction temperature is from room temperature to 50° C.

2) Scheme B

When $X^1$ is a nitrogen atom, and $R^4$ is —$COOR^c$ or —$CONHSO_2$—($C_1$-$C_6$ alkyl), a pyrazine derivative can be synthesized as shown in the following Scheme B. That is, after a compound (B-3) is obtained by an imidazole ring formation reaction using a compound (B-1) and a compound (B-2), a compound (B-4) is obtained by N-alkylation of the compound (B-3) using a base and a halide compound or by a Mitsunobu reaction using an alcohol. When necessary, by hydrolyzing an ester group of the compound (B-4) in a similar manner as in Scheme A, there can be obtained a compound (B-5). Further, when $R^3$ is a hydrogen atom, another synthetic route is possible. That is, by an N-alkylation reaction of a compound (B-6), which can be synthesized easily, a compound (B-7) is obtained, which is subsequently converted to a compound (B-8) by a bromination reaction, followed by a CO insertion reaction thereof using palladium in an alcohol to obtain the compound (B-4).

Scheme B

[Chemical formula 10]

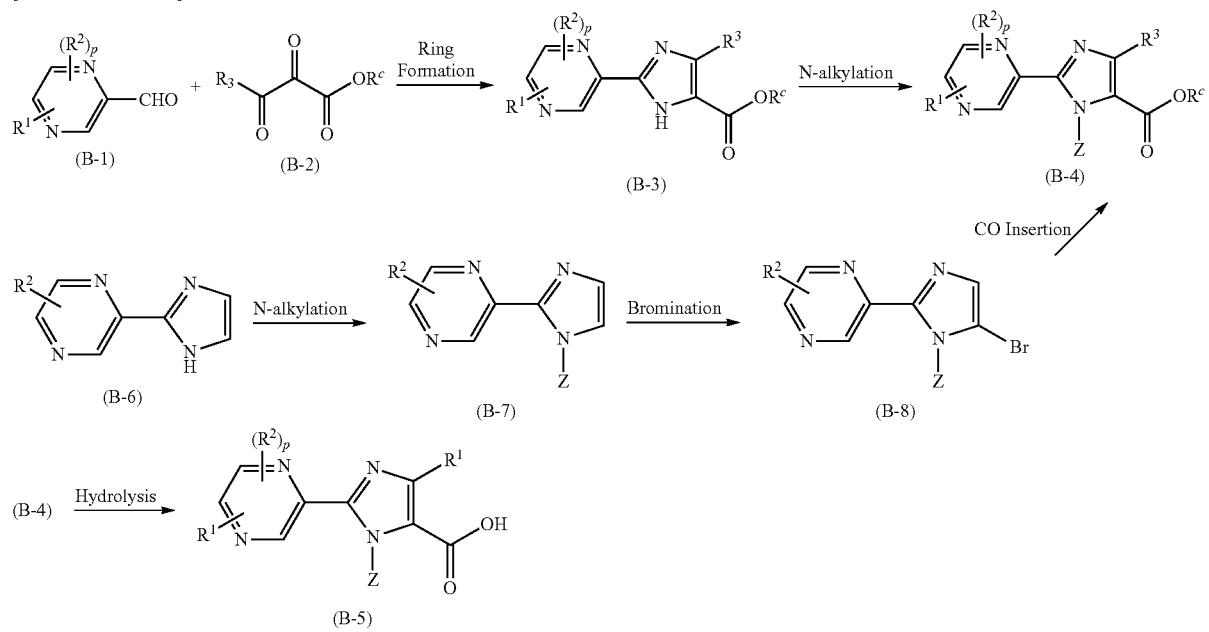

Here, in the imidazole ring formation reaction using the compound (B-1) and the compound (B-2), the reaction proceeds by heating the compound (B-1) and the compound (B-2) in, for example, acetic acid in the presence of 2 equivalents or more, or preferably 10 equivalents or more of ammonium acetate. The reaction temperature for the present reaction is preferably from room temperature to 150° C., but it is more preferable to carry out the reaction from 50° C. to 120° C. The N-alkylation reaction of the compound (B-3) and the hydrolysis reaction of the compound (B-4) are preferably carried out under the conditions described in Scheme A.

The N-alkylation reaction of the compound (B-6) to form the compound (B-7) and the bromination reaction of the compound (B-7) to form the compound (B-8) are preferably carried out under the conditions described in Scheme A. The CO insertion reaction of the compound (B-8) to form the compound (B-4) proceeds by heating the mixture of a palladium catalyst, a base, and the compound (B-8) in an alcoholic solvent in a CO atmosphere. With regard to the alcoholic solvent, preferable is methanol or ethanol. As regards the palladium catalyst, preferable is [1,1'-bis(diphenylphosphino)ferrocene]dichloropalladium(II) (PdCl$_2$(dppf)), tetrakis(triphenylphosphine)palladium (Pd(PPh$_3$)4), or the like. The base is preferably triethylamine or diisopropylethylamine. The reaction temperature for the reaction is preferably from room temperature to 150° C., and more preferably from 50° C. to 90° C.

3) Scheme C

When $X^1$ is a carbon atom, $R^3$ is a hydrogen atom or a $C_1$-$C_6$ alkyl group, and $R^4$ is —COOR$^c$ or acrylic acid, a pyrazine derivative can be synthesized as shown in the following Scheme C. That is, in the case where $R^4$ is a carboxylic acid, after obtaining a compound (C-2) by N-alkylation of a heretofore known pyrrole derivative (C-1), a Stille coupling reaction thereof with 2-(tributylstannyl) pyrazine derivative provides a compound (C-3). By a subsequent oxidation reaction, a target compound (C-4) can be obtained. If necessary, by carrying out a condensation reaction of the compound (C-4) with an alkylsulfonamide, there can be obtained an acylsulfonamide entity (C-5). Further, when $R^4$ is acrylic acid, the compound (C-3) is subjected to a Horner-Emmons reaction to obtain a compound (C-6). By hydrolyzing the compound, there can be obtained a compound (C-7).

Scheme C

[Chemical formula 11]

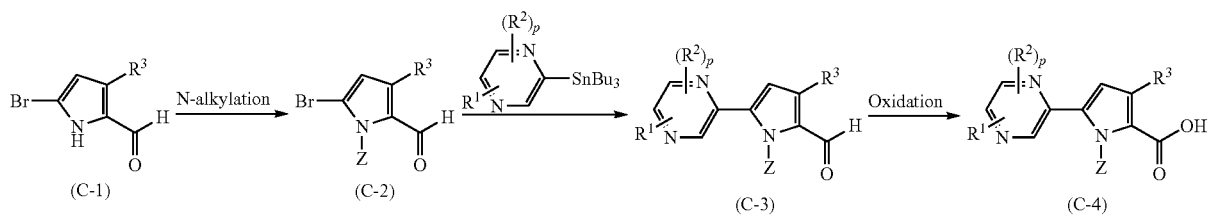

-continued

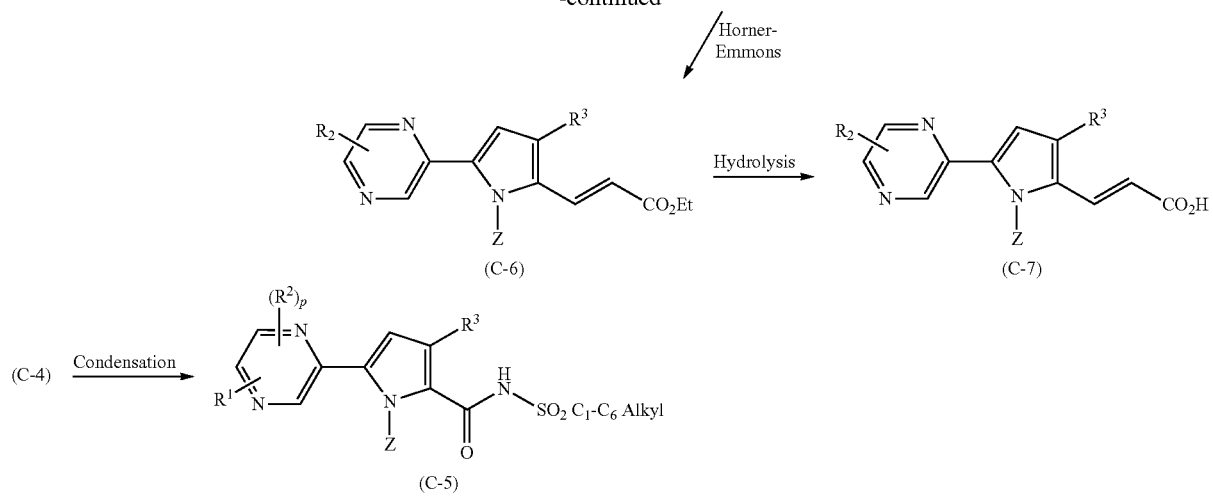

In Scheme C, the N-alkylation reaction of the compound (C-1) to form the compound (C-2) and the subsequent Stille coupling reaction of the compound (C-2) are preferably carried out under the conditions described in Scheme A. Further, with regard to the oxidation reaction of the compound (C-3), there is widely known a Pinnick oxidation reaction and the reaction is carried out preferably under the conditions where sodium chlorite and sodium dihydrogen phosphate are used in the presence of 2-methyl-2-butene. As a reaction solvent, it is preferable to use a mixed solvent of tetrahydrofuran or an alcohol such as tert-butanol and propanol with water. Furthermore, the reaction temperature is preferably from room temperature to 50° C. The Horner-Emmons reaction to form the compound (C-6) from the compound (C-3) proceeds by mixing the compound (C-3) and ethyl diethylphosphonoacetate in THF in the presence of a base such as sodium hydride, nBuLi, or the like. The reaction temperature is preferably from 0° C. to room temperature. The subsequent hydrolysis is preferably conducted under the conditions described in Scheme A.

4) Scheme D

When $X^1$ is a nitrogen atom, $R^4$ is a tetrazolyl group, acrylic acid, or thiomethypropanoic acid, synthesis of a pyrazine derivative can be carried out as shown in the following Scheme D. That is, in the case of a tetrazole entity, a cyano group is introduced to a compound (D-1) which can be obtained by the same method as that for the compound (B-8) described in the Scheme B by using palladium to obtain a compound (D-2), whose cyano group is subsequently converted to a tetrazolyl group by using sodium azide to obtain a compound (D-3). In the case where $R^4$ is acrylic acid, the compound (D-1) is subjected to a Heck reaction to obtain a compound (D-4) and subsequent hydrolysis reaction can yield a compound (D-5). In the case where $R^4$ is a thiomethylpropanoic acid, after introducing an SH group to the compound (D-1) using palladium to obtain a compound (D-6), S-alkylation thereof is performed to obtain a compound (D-7). Finally, a compound (D-8) can be obtained by hydrolysis of the same.

Scheme D

[Chemical formula 12]

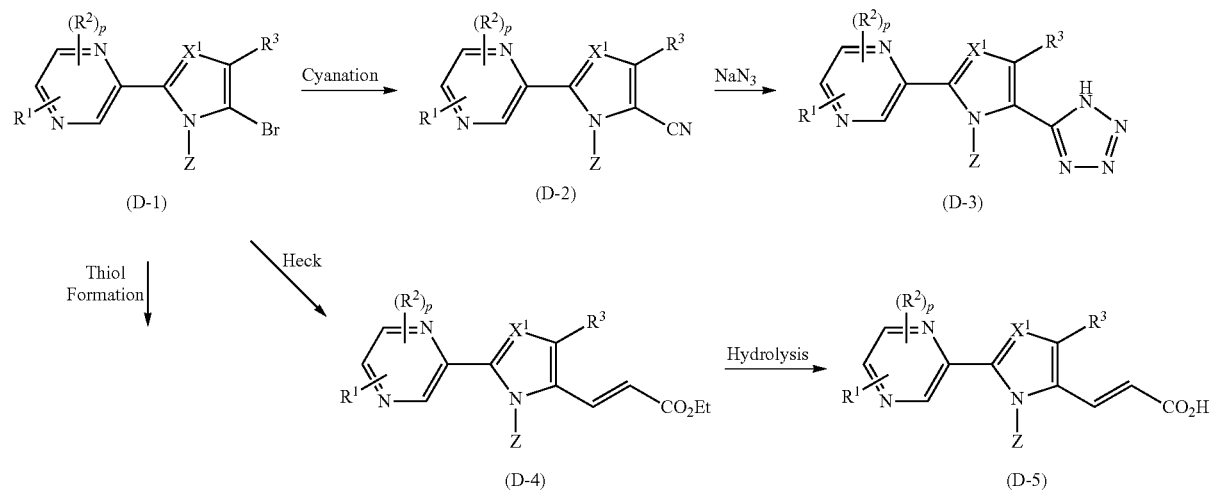

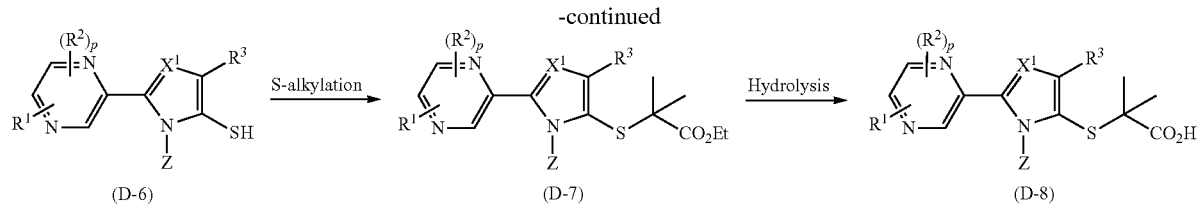

The cyanation reaction of the compound (D-1) to form the compound (D-2) is preferably conducted in DMF under the conditions where the compound (D-1) is heated in the presence of a palladium catalyst such as [1,1'-bis(diphenylphosphino)ferrocene]dichloropalladium(II) (PdCl$_2$(dppf)), tetrakis(triphenylphosphine)palladium (Pd(PPh$_3$)4), or the like, and Zn(CN)$_2$. The reaction proceeds from 50° C. to 150° C., but the reaction temperature is preferably from 80° C. to 100° C. Conversion from the compound (D-2) to the compound (D-3) is preferably carried out under the conditions using triethylamine hydrochloride and sodium azide in DMF. The reaction proceeds from 100° C. to 170° C., but the reaction temperature is preferably from 120° C. to 150° C.

The Heck reaction of the compound (D-1) to form the compound (D-4) proceeds under the conditions where the compound (D-1) and an acrylic acid ester are heated in acetonitrile or an amide-based solvent such as DMF, DMA, or the like using a palladium catalyst such as [1,1'-bis(diphenylphosphino)ferrocene]dichloropalladium(II) (PdCl$_2$(dppf)), tetrakis(triphenylphosphine)palladium (Pd(PPh$_3$)$_4$) and the like, a base such as potassium carbonate, triethylamine, diisopropylethylamine, or the like. The reaction proceeds at room temperature to 150° C., but the reaction temperature is preferably from 80° C. to 140° C. The hydrolysis is preferably performed under the conditions described in Scheme A.

The introduction of an SH group to the compound (D-1) to obtain the compound (D-6) is conducted in accordance with an article in Org. Lett., 2004, 6, 4587-4590 or Org. Lett., 2007, 9, 3687-3689 as reference by introducing an alkylthio moiety by heating, under a nitrogen atmosphere, the compound (D-1) in 1,4-dioxane, in the presence of 2-ethylhexyl 3-mercaptopropionate, Pd$_2$(dba)$_3$, Xantphos and diisopropylethylemine. By subsequently carrying out a beta-elimination reaction under a basic condition, there can be obtained the compound (D-6). With regard to the beta-elimination reaction, the reaction is preferably carried out under the conditions where a small excess amount of KOtBu is used in DMF at room temperature. The S-alkylation of the compound (D-6) to form the compound (D-7) is preferably carried out under the same condition as the N-alkylation in Scheme A, and more preferably under the conditions where a base and a halide compound are used. As for the hydrolysis of the compound (D-7), it is preferably performed under the conditions described in Scheme A.

The pyrazine derivative represented by formula (I) and the pharmaceutically acceptable salt thereof, and the solvate thereof of the present invention can be used as a URAT1 inhibitor. Furthermore, as a clinically applicable URAT1 inhibitor, these can be used as a preventive agent or a therapeutic agent for a disease selected from the group consisting of gout, hyperuricemia, hypertension, kidney diseases such as interstitial nephritis and the like, diabetes, arteriosclerosis, and Lesch-Nyhan syndrome.

The therapeutic agent or a preventive agent for gout, hyperuricemia, and the like containing the pyrazine derivative or the pharmaceutically acceptable salt thereof, or the solvate thereof of the present invention is prepared using a carrier, an excipient, and other additives which are commonly used in formulation. The carrier and the excipient for formulation may be either solid or liquid and include, for example, lactose, magnesium stearate, starch, talc, gelatin, agar, pectin, gum arabic, olive oil, sesame oil, cocoa butter, ethylene glycol, and others in common use. Administration may be in any form of either oral administration by means of tablets, pills, capsules, granules, powder, fluids, and the like; or parenteral administration by means of injections such as intravenous injections, intramuscular injections, and the like, suppositories, percutaneous agents, and the like.

In the present invention, "prevention" refers to preventing incidence or onset in an individual who has not yet contracted or developed a disease, and "therapy" refers to cure, suppress, or improve diseases or symptoms in an individual who has already contracted or developed a disease.

An effective dose of the active ingredient in the URAT1 inhibitor, the therapeutic agent, or the preventive agent of the present invention varies depending on the route of administration, ages and gender of the patients, the degree of disease, but is generally about 0.1 to 100 mg/day, and the number of dose is 1 to 3 times a day and 1 to 7 times a week. The formulation is preferably prepared to satisfy these conditions. However, because the dose varies depending on various conditions, there are cases where a less amount than the above dose is sufficient or there are cases where a dose exceeding the above range is necessary.

EXAMPLES

In the following, the present invention will be described in more detail by way of Examples but the present invention is not limited by these. Further, abbreviations in the present invention are as follows:
DMF=N,N-dimethylformamide;
THF=tetrahydrofuran;
NBS=N-bromosuccinimide;
NCS=N-chlorosuccinimide;
DEAD=diethyl azodicarboxylate;
DIAD=diisopropyl azodicarboxylate;
PdCl$_2$(dppf)=[1,1'-bis(diphenylphosphino)ferrocene]dichloropalladium(II);
PdCl$_2$(dppf).CH$_2$Cl$_2$=[1,1'-bis(diphenylphosphino)ferrocene]dichloropalladium(II)-CH$_2$Cl$_2$ complex;
BSA=N,O-bis(trimethylsilyl)acetamide; and
AIBN=2,2'-azobis(isobutyronitrile).

Structures of isolated new compounds were confirmed by $^1$H-NMR and/or mass spectrometry using single quadrupole instrumentation equipped with an electrospray ionization source, and other appropriate analytical methods.

For compounds whose $^1$H-NMR spectra (400 MHz, DMSO-d$_6$, CDCl$_3$, or CD$_3$OD) were measured, the chemical shifts (δ: ppm) and the coupling constants (J: Hz) thereof are presented. The results of mass spectrometry present

[M+H]+, namely a measured value observed as a value corresponding to a molecular mass (M) of a compound to which a mass of a proton (H+) is added. Further, [M−H]− shows a measured value corresponding to a molecular mass (M) of a compound from which a mass of a proton (H+) is subtracted. In addition, the following abbreviations indicate those indicated respectively: s=singlet, d=doublet, t=triplet, q=quartet, brs=broad singlet, and m=multiplet.

Compounds synthesized in accordance with methods of the following Examples were further analyzed by a high-performance liquid chromatography (HPLC) analysis and by mass spectrometry using a time of flight mass spectrometer (TOF-MS) equipped with an electrospray ionization source.

A retention time (unit:minute) of a compound in the HPLC analysis under the following analytical conditions is presented as an HPLC retention time.
Conditions of HPLC measurement:
the instrument: Hewlett-Packard 1100 HPLC;
column: Imtakt Cadenza CD-C18 100 mm×4.6 mm, 3 μm;
UV: PDA detection (254 nm);
column temperature: 40° C.;
gradient conditions:
  solvent A: $H_2O$/acetnitrile=95/5
    0.05% TFA (trifluoroacetic acid)
  B: $H_2O$/acetonitrile=5/95
    0.05% TFA (trifluoroacetic acid)
  flow rate: 1.0 mL/minute
  gradient: 0 to 1 minute: solvent B, 2%; solvent A, 98%
    1 to 14 minutes: solvent B, 2% to 100%; solvent A, 98% to 0%
    14 to 17 minutes: solvent B, 100%; solvent A, 0%
    17 to 19 minutes: solvent B, 100% to 2%; solvent A, 0% to 98%.

Further, with regard to the results of mass spectrometry, there is shown in addition to the value of [M+H]+ (Obs. Mass, namely a measured value of a molecular mass (M) of a molecule plus the mass of a proton [H+]), a calculated value of the [M+H]+ (Pred. Mass) and, at the same time, a compositional formula (Formula) calculated from the measured value of [M+H]+. Furthermore, is some cases, there is shown in addition to the value of [M−H]− (Obs. Mass: namely a measured value of a molecular mass (M) of a molecule minus the mass of a proton [H+]), a calculated value of the [M−H]− (Pred. Mass) and, at the same time, a compositional formula (Formula) calculated from the measured value of [M−H]−.
Conditions of TOF-MS measurement:
mass spectrometer: LCMS-IT-POF manufactured by Shimadzu Corporation;
LC: Prominence;
column: Phenomenex Synergi Hydro-RP 4.0 mm×20 mm, 2.5 μm;
UV: PDA detection (254 nm);
flow rate: 0.6 mL/minute;
column temperature: 40° C.;
detecting voltage: 1.63 kV (when detecting [M+H]+), −1.63 kV (when detecting [M−H]−);
gradient conditions:
  solvent A: $H_2O$/acetnitrile=95/5
    0.1% $HCO_2H$
  B: $H_2O$/acetonitrile=5/95
    0.1% $HCO_2H$
  flow rate: 0.5 mL/minute
  gradient: 0 to 0.2 minute: solvent B, 2%; solvent A, 98%
    0.2 to 2.5 minutes: solvent B, 2% to 100%; solvent A, 98% to 0%
    2.5 to 3.8 minutes: solvent B, 100%; solvent A, 0%
    3.8 to 4.0 minutes: solvent B, 100% to 2%; solvent A, 0% to 98%
    4.0 to 5.0 minutes: solvent B, 2%; solvent A, 98%.

Example 1

Synthesis of 1-(2,5-dichlorobenzyl)-4-methyl-2-(pyrazin-2-yl)-1H-imidazole-5-carboxylic acid (Compound A1) (Scheme A)

[Chemical formula 13]

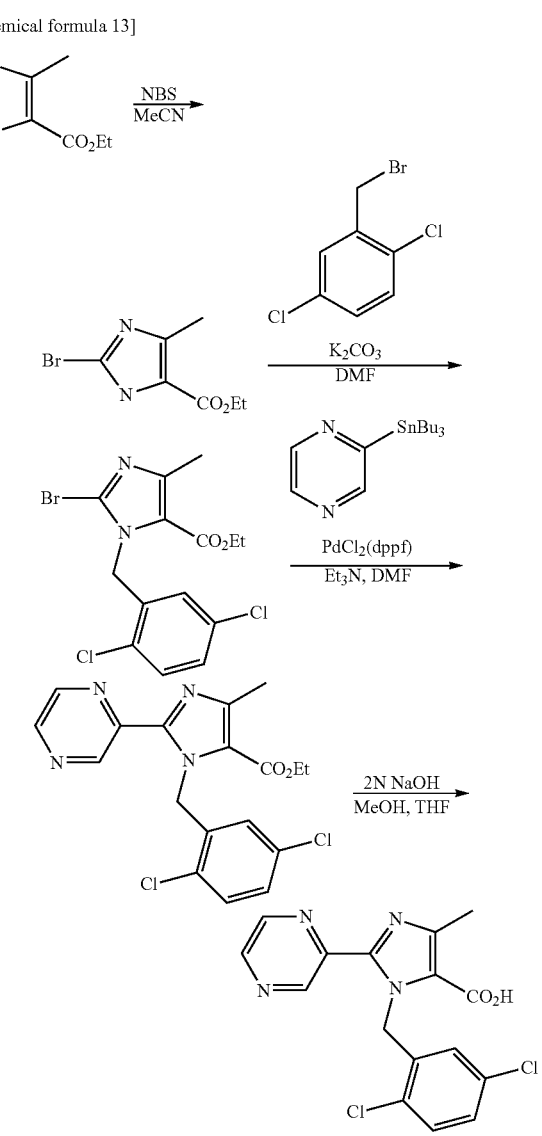

Ethyl 5-methyl-1H-imidazole-4-carboxylate (produced by Sigma-Aldrich Co.) (7.5 g, 48.7 mmol) was dissolved in acetonitrile (120 mL), N-bromosuccinimide (10.4 g, 58.4 mmol) was added thereto, and the reaction mixture was stirred at room temperature for 3 hours. After the reaction was complete, a saturated aqueous sodium bicarbonate solution was added, and the reaction mixture was extracted twice with ethyl acetate. The organic layer was washed with a saturated aqueous sodium chloride solution and, thereafter, dried over anhydrous sodium sulfate. After concentration, the residue was purified by silica gel column chromatography to obtain ethyl 2-bromo-4-methyl-1H-imidazole-5-carboxylate (3.6 g): 1H-NMR (CDCl$_3$) δ: 4.35 (2H, q, J=7.1 Hz), 2.51 (3H, s), 1.37 (3H, t, J=7.1 Hz); ESI-MS m/z=233 (M+H)$^+$.

2) Ethyl 2-bromo-4-methyl-1H-imidazole-5-carboxylate (2.75 g, 11.8 mmol) was dissolved in DMF (20 mL), potassium carbonate (3.26 g, 23.6 mmol) and 2,5-dichloronbenzyl bromide (3.4 g, 14.2 mmol) were added thereto, and the reaction mixture was stirred at 90° C. for 3 hours. Water (50 mL) was added after the reaction was complete, and the reaction mixture was extracted twice with ethyl acetate (50 mL). After washing with a saturated aqueous sodium chloride solution, the organic phase was dried over sodium sulfate. After concentration under reduced pressure, the residue was purified by silica gel column chromatography to obtain ethyl 2-bromo-1-(2,5-dichlorobenzyl)-4-methyl-1H-imidazole-5-carboxylate (1.72 g): $^1$H-NMR (CDCl$_3$) δ: 7.34 (1H, d, J=8.8 Hz), 7.20 (1H, dd, J=8.8, 2.4 Hz), 6.40 (1H, d, J=2.4 Hz), 5.60 (2H, s), 4.25 (2H, q, J=7.2 Hz), 2.56 (3H, s), 1.27 (3H, t, J=7.1 Hz); ESI-MS m/z=391 (M+H)$^+$.

(3) Ethyl 2-bromo-1-(2,5-dichlorobenzyl)-4-methyl-1H-imidazole-5-carboxylate (80 mg, 0.204 mmol), 2-(tributylstannyl)pyrazine (produced by Wako Pure Chemical Ind., Ltd.) (151 mg, 0.409 mmol), PdCl$_2$(dppf) (44.8 mg, 0.061 mmol), and cesium carbonate (133 mg, 0.408 mmol) were dissolved in 1,4-dioxane (1 mL), and the resultant solution was stirred under a nitrogen atmosphere at 100° C. for 18 hours. Water (50 mL) was added after the reaction was complete, and the reaction mixture was extracted twice with ethyl acetate (50 mL). After washing with a saturated aqueous sodium chloride solution, the organic phase was dried over sodium sulfate. After concentration, the residue was purified by silica gel column chromatography to obtain ethyl 1-(2,5-dichlorobenzyl)-4-methyl-2-(pyrazin-2-yl)-1H-imidazole-5-carboxylate (7.6 mg): $^1$H-NMR (CDCl$_3$) δ: 9.49 (1H, d, J=1.5 Hz), 8.50 (1H, d, J=2.4 Hz), 8.41-8.39 (1H, m), 7.31 (1H, d, J=8.8 Hz), 7.13 (1H, dd, J=8.8, 2.4 Hz), 6.46 (1H, d, J=2.4 Hz), 6.23 (2H, s), 4.28 (2H, q, J=7.2 Hz), 2.65 (3H, s), 1.30 (3H, t, J=7.1 Hz); ESI-MS m/z=391 (M+H)$^+$.

(4) Ethyl 1-(2,5-dichlorobenzyl)-4-methyl-2-(pyrazin-2-yl)-1H-imidazole-5-carboxylate (7.6 mg) was dissolved in a mixed solvent of THF (1 mL) and methanol (1 mL), a 2M aqueous sodium hydroxide solution (0.2 mL, 0.4 mmol) was added thereto, and the reaction mixture was heated and stirred at 50° C. for 3 hours. After cooling the reaction mixture to room temperature, 2M hydrochloric acid (0.2 mL, 0.4 mmol) was added, and the mixture was concentrated under reduced pressure. A residue obtained after concentration was purified by a usual method to obtain 1-(2,5-dichlorobenzyl)-4-methyl-2-(pyrazin-2-yl)-1H-imidazole-5-carboxylic acid (Compound A1, 3.99 mg): $^1$H-NMR (DMSO-d$_6$) δ: 13.19 (1H, s), 9.32 (1H, s), 8.61 (1H, d, J=2.4 Hz), 8.54-8.51 (1H, m), 7.52 (1H, d, J=8.3 Hz), 7.33 (1H, dd, J=8.5, 2.2 Hz), 6.42 (1H, s), 6.12 (2H, s), 2.52 (3H, s); HPLC retention time=10.02 min; Pred. Mass=363.0410 (M$^+$+H, C$_{16}$H$_{12}$Cl$_2$N$_4$O$_2$); Obs. Mass=363.0399 (M$^+$+H).

Example 2

Synthesis of 1-(2,5-dichlorobenzyl)-4-methyl-2-(pyrazin-2-yl)-1H-imidazole-5-carboxylic acid (Compound A1) (Scheme B)

[Chemical formula 14]

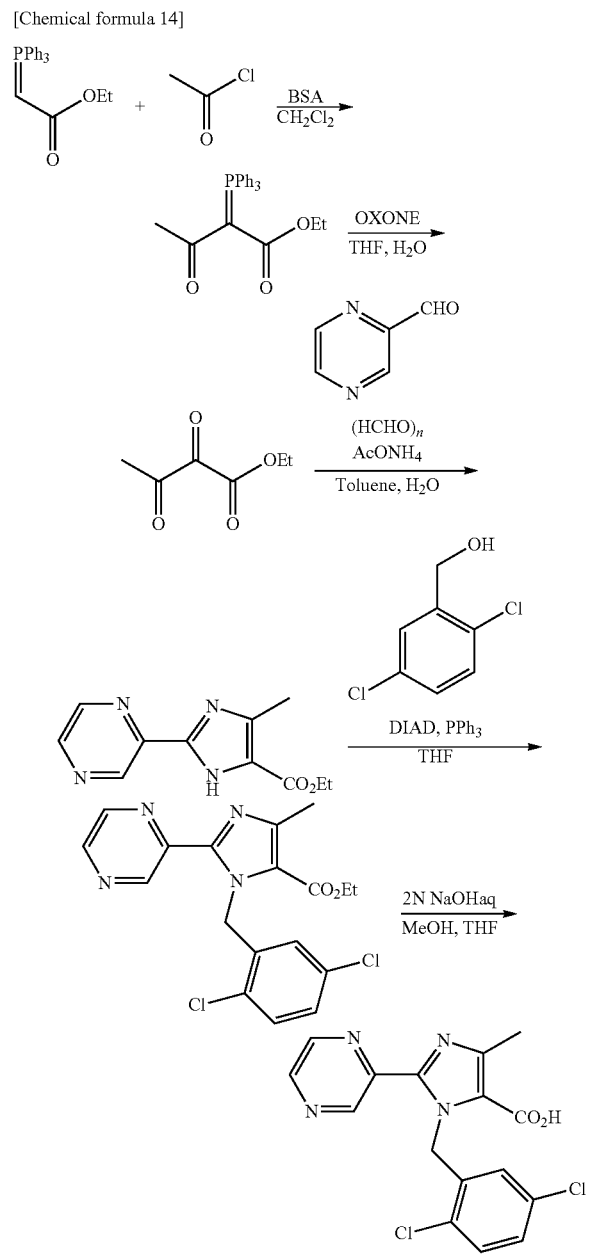

(1) Ethyl 2-(triphenylphosphoranylidene)acetate (produced by Wak Pure Chemical Ind., Ltd.) (11.1 g, 31.9 mmol) was dissolved in dichloromethane (100 mL), acetyl chloride (produced by Wako Pure Chemical Ind., Ltd.) (2.5 mL, 35.0 mmol) and N,O-bis(trimethylsilyl)acetamide (BSA) (9.74 mL, 40.0 mmol) were added thereto under ice cooling, and the reaction mixture was stirred at room temperature for 1 hour. Water (100 mL) was added after the reaction was complete, and the aqueous phase was extracted twice with dichloromethane. After washing with a saturated aqueous sodium chloride solution, the organic phase was dried over anhydrous magnesium sulfate. After concentration under reduced pressure, the residue was purified by silica gel column chromatography to obtain ethyl 3-oxo-2-(triphenylphosphoranylidene)butanoate (6.63 g):

1H-NMR (CDCl$_3$) δ: 7.68-7.63 (6H, m), 7.53-7.41 (9H, m), 3.73 (2H, q, J=7.0 Hz), 2.46 (3H, s), 0.66 (3H, t, J=7.1 Hz); ESI-MS m/z=391 (M+H)$^+$.

(2) Ethyl 3-oxo-2-(triphenylphophoranylidene)butanoate (6.63 g, 17.0 mmol) was dissolved in tetrahydrofuran (70 mL) and water (50 mL), potassium peroxymonosulfate (OXONE) (12.5 g, 20.3 mmol) was added thereto under ice cooling, and the reaction mixture was stirred at room temperature for 16 hours. After the reaction was complete, tetrahydrofuran was distilled off under reduced pressure, and the aqueous phase was extracted three times with ethyl acetate (100 mL). The organic phase was dried over anhydrous magnesium sulfate, and a residue obtained by concentration was purified by silica gel column chromatography to obtain ethyl 2,3-dioxobutanoate (1.29 g): $^1$H-NMR (CDCl$_3$) δ: 4.33 (2H, q, J=7.2 Hz), 2.30 (3H, s), 1.32 (3H, t, J=7.1 Hz).

(3) Ethyl 2,3-dioxobutanoate (2.9 g, 20.0 mmol), pyrazine aldehyde (2.02 g, 18.7 mmol), and ammonium acetate (14.4 g, 187 mmol) were dissolved in toluene (35 mL) and water (7 mL), and the reaction mixture was heated under stirring at 70° C. for 3 hours. After the reaction was complete, toluene was concentrated, water was added to the residue, and a solid which precipitated was collected by filtration to obtain ethyl 4-methyl-2-(pyrazin-2-yl)-1H-imidazole-5-carboxylate (1.62 g): ESI-MS m/e=233 (M+H)$^+$.

(4) Ethyl 4-methyl-2-(pyrazin-2-yl)-1H-imidazole-5-carboxylate (647 mg, 2.78 mmol), 2,5-dichlorobenzyl alcohol (740 mg, 4.18 mmol), and triphenylphosphine (1.1 g, 4.19 mmol) were dissolved in THF (10 mL), DEAD (a 40% solution, 1.5 mL, 4.18 mmol) was added thereto dropwise at 0° C. under cooling, and the reaction mixture was stirred at 50° C. for 1 hour. The solvent was distilled off under reduced pressure, and the residue was purified by silica gel column chromatography to obtain ethyl 1-(2,5-dichlorobenzyl)-4-methyl-2-(pyrazin-2-yl)-1H-imidazole-5-carboxylate (1.0 g): $^1$H-NMR (CDCl$_3$) δ: 9.49 (1H, d, J=1.5 Hz), 8.50 (1H, d, J=2.4 Hz), 8.41-8.39 (1H, m), 7.31 (1H, d, J=8.8 Hz), 7.13 (1H, dd, J=8.8, 2.4 Hz), 6.46 (1H, d, J=2.4 Hz), 6.23 (2H, s), 4.28 (2H, q, J=7.2 Hz), 2.65 (3H, s), 1.30 (3H, t, J=7.1 Hz); ESI-MS m/z=391 (M+H)$^+$.

By finally hydrolyzing this compound under the conditions described in Example 1, A1 can be synthesized in the similar manner Example 3

Synthesis of 1-(2,5-dichlorobenzyl)-2-(pyrazin-2-yl)-1H-pyrrole-5-carboxylic acid (Compound A15) (Scheme C)

[Chemical formula 15]

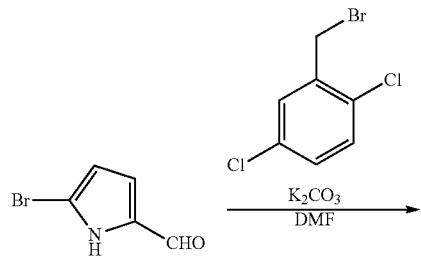

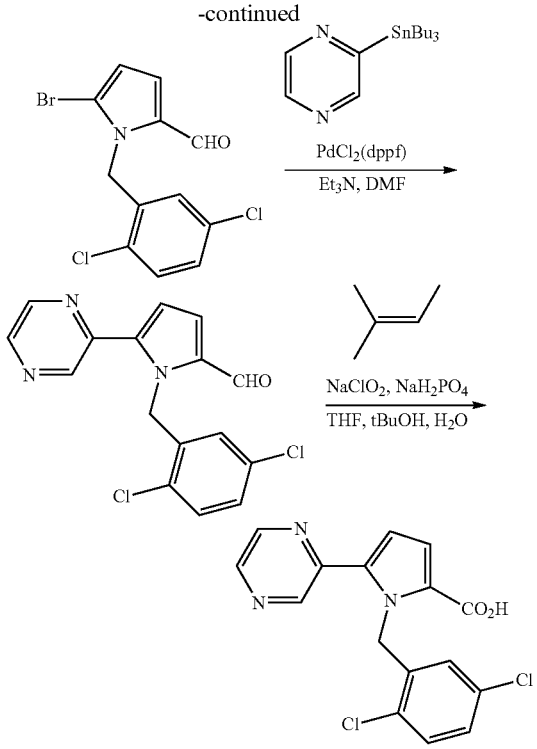

(1) 2-Bromo-1H-pyrrole-5-carbaldehyde (1 g, 5.75 mmol) which is described in literature (for example, Can. J. Chem., 1995, 73, 675-684) and 2,5-dichlorobenzyl bromide (1.8 g, 7.47 mmol) were dissolved in DMF (5 mL). Potassium carbonate (1.59 g, 11.49 mmol) was added thereto, and the reaction mixture was heated and stirred at 90° C. for 3 hours. Water was added after cooling, and the reaction mixture was extracted twice with ethyl acetate. The organic phase was washed with a saturated aqueous sodium chloride solution, dried over anhydrous magnesium sulfate, and concentrated under reduced pressure. The residue obtained was purified by silica gel column chromatography to obtain 2-bromo-1-(2,5-dichlorobenzyl)-1H-pyrrole-5-carbaldehyde (1.8 g): $^1$H-NMR (CDCl$_3$) δ: 9.40 (1H, s), 7.32 (1H, d, J=8.8 Hz), 7.17 (1H, dd, J=8.8, 2.4 Hz), 7.05 (1H, d, J=3.9 Hz), 6.48 (1H, d, J=3.9 Hz), 6.22 (1H, d, J=2.4 Hz), 5.74 (2H, s); ESI-MS m/z=332 (M+H)$^+$.

(2) A reaction mixture was prepared by adding dioxane (1 mL) to 2-bromo-1-(2,5-dichlorobenzyl)-1H-pyrrole-5-carbaldehyde (150 mg, 0.45 mmol), 2-(tributylstannyl)pyrazine (produced by Wako Pure Chemical Ind., Ltd.) (249 mg, 0.676 mmol), cesium carbonate (294 mg, 0.90 mmol), and PdCl$_2$ (dppf) (82 mg, 0.113 mmol). The reaction mixture was heated and stirred at 100° C. for 5 hours. Water was added after cooling, and the reaction mixture was extracted twice with ethyl acetate. Subsequently, the organic phase was washed with a saturated aqueous sodium chloride solution, dried over anhydrous magnesium sulfate, and then concentrated under reduced pressure. The residue obtained was purified by silica gel column chromatography to obtain 1-(2,5-dichlorobenzyl)-2-(pyrazin-2-yl)-1H-pyrrole-5-carbaldehyde (64 mg): ESI-MS m/z=332 (M+H)$^+$.

(3) 1-(2,5-Dichlorobenzyl)-2-(pyrazin-2-yl)-1H-pyrrole-5-carbaldehyde (64 mg, 0.193 mmol) and 2-methyl-2-butene (95 mg, 1.35 mmol) were dissolved in a mixed solvent of THF (1 mL) and tert-butanol (1 mL), and an aqueous solution (2 mL) of a mixture of sodium chlorite (148 mg, 1.64 mmol) and sodium dihydrogenphosphate dihydrate (195 mg, 1.25 mmol) was dropwise added thereto to prepare a reaction mixture. The reaction mixture was stirred at room temperature for 4 hours. A saturated aqueous sodium chloride solution was added after the reaction was complete, and the reaction mixture was extracted twice with ethyl acetate. The organic phase was dried over anhydrous magnesium sulfate, and was subsequently concentrated under reduced pressure. The residue obtained was purified by HPLC to obtain 1-(2,5-dichlorobenzyl)-2-(pyrazin-2-yl)-1H-pyrrole-5-carboxylic acid (38 mg): $^1$H-NMR (DMSO-$d_6$) δ: 12.70 (1H, s), 9.08 (1H, s), 8.47 (2H, s), 7.47 (1H, d, J=8.3 Hz), 7.28 (1H, dd, J=8.5, 2.2 Hz), 7.16-7.08 (2H, m), 6.19-6.13 (3H, m); HPLC retention time=11.28 min; Pred. Mass=348.0301 ($M^+$+H, $C_{16}H_{11}Cl_2N_3O_2$); Obs. Mass=348.0299 ($M^+$+H).

Examples 4 to 16

The compounds with compound number A2 to A14 were synthesized with reference to any of the Example 1 to Example 3, and synthetic methods of Schemes A to D described in the general synthesis section.

TABLE 3

| Compound Number | HPLC Retention Time | Obs. Mass [M + H]$^+$ | Pred. Mass [M + H]$^+$ | Formula (M) | $^1$H NMR |
|---|---|---|---|---|---|
| A2 | 10.37 | 377.0565 | 377.0567 | $C_{17}H_{14}Cl_2N_4O_2$ | (DMSO-d6) δ: 13.2 (1H, s), 9.11 (1H, s), 8.50 (1H, s) 7.56 (1H, d, J = 8.6 Hz), 7.34 (1H, dd, J = 8.5 Hz, 2.4 Hz, 6.41 (1H, d, J = 2.2 Hz, 6.11 (2H, s), 2.54 (3H, s), 2.29 (3H, s). |
| A3 | 11.03 | 389.0591 [M − H]$^-$ | 389.0578 [M − H]$^-$ | $C_{18}H_{16}Cl_2N_4O_2$ | (DMSO-d6) δ: 13.2 (1H, s), 9.14 (1H, s), 8.53 (1H, s) 7.56 (1H, d, J = 8.6 Hz), 7.36 (1H, dd, J = 8.4 Hz, 2.3 Hz, 6.40 (1H, d, J = 2.1 Hz, 6.08 (2H, s), 2.61 (2H, q, J = 7.5 Hz), 2.54 (3H, s), 0.87 (3H, t, J = 7.5 Hz). |
| A4 | 11.96 | 437.0574 [M − H]$^-$ | 437.0578 [M − H]$^-$ | $C_{22}H_{16}Cl_2N_4O_2$ | (DMSO-d6) δ: 13.0 (1H, s), 9.05 (1H, s), 8.58 (1H, s) 7.35 (1H, d, J = 8.5 Hz), 7.24 (1H, d, J = 8.6 Hz, 7.16-7.11 (2H, m), 7.02-6.98 (3H, m), 6.13 (1H, s), 5.70 (2H, s), 2.45 (3H, s). |
| A5 | 10.45 | 393.052 | 393.0516 | $C_{17}H_{14}Cl_2N_4O_3$ | (DMSO-d6) δ: 8.88 (1H, s), 8.28 (1H, s), 7.53 (1H, d, J = 8.4 Hz), 7.37 (1H, d, J = 8.6 Hz), 6.39 (1H, s), 6.09 (2H, s), 3.37 (3H, s), 2.52 (3H, s). |
| A6 | 11.96 | 455.0667 | 455.0672 | $C_{22}H_{16}Cl_2N_4O_3$ | (DMSO-d6) δ: 13.2 (1H, s), 9.28 (1H, s), 9.26 (1H, s), 7.66-7.58 (3H, m), 7.47-7.41 (2H, m), 7.37-7.32 (2H, m), 6.51 (1H, s), 6.07 (2H, s), 2.57 (3H, s). |
| A7 | 11.04 | 407.0662 | 407.0672 | $C_{18}H_{16}Cl_2N_4O_3$ | (DMSO-d6) δ: 13.1 (1H, s), 8.87 (1H, s), 8.27 (1H, s) 7.57 (1H, d, J = 8.6 Hz), 7.39 (1H, dd, J = 8.4 Hz, 2.2 Hz, 6.44 (1H, d, J = 1.9 Hz, 5.99 (2H, s), 3.68 (2H, q, J = 7.1 Hz), 2.53 (3H, s), 1.02 (3H, t, J = 7.0 Hz). |
| A8 | 10.77 | 386.0211 [M − H]$^-$ | 386.0217 [M − H]$^-$ | $C_{17}H_{11}Cl_2N_5O_2$ | (DMSO-d6) δ: 13.4 (1H, s), 9.53 (1H, s), 9.10 (1H, s) 7.56 (1H, d, J = 8.5 Hz), 7.35 (1H, dd, J = 8.5 Hz, 2.3 Hz, 6.45 (1H, s),6.10 (2H, s), 2.55 (3H, s). |
| A9 | 11.54 | 405.0875 | 405.088 | $C_{19}H_{18}Cl_2N_4O_2$ | (DMSO-d6) δ: 13.1 (1H, s), 9.16 (1H, s), 8.55 (1H, s) 7.57 (1H, d, J = 8.3 Hz), 7.37 (1H, d, J = 8.3 Hz), 6.39 (1H, s), 6.04 (2H, s), 2.97-2.91 (1H, m), 2.54 (3H, s), 0.88 (6H, d, J = 6.8 Hz). |
| A10 | 10.92 | 403.0723 | | $C_{19}H_{16}Cl_2N_4O_2$ | (DMSO-d6) δ: 13.1 (1H, s), 9.06 (1H, s), 8.63 (1H, s) 7.59 (1H, d, J = 8.6 Hz), 7.40 (1H, d, J = 8.6 Hz, 6.35 (1H, s), 5.92 (2H, s), 2.52 (3H, s), 2.08-2.05 (1H, m), 0.81-0.77 (2H, m), 0.27-0.25 (2H, m). |
| A11 | 10.15 | 368.9968 | 368.9974 | $C_{14}H_{10}Cl_2N_4O_2S$ | (DMSO-d6) δ: 13.23 (1H, s), 9.28 (1H, d, J = 1.0 Hz), 8.66-8.65 (2H, m), 6.51 (1H, s), 5.99 (2H, s), 2.47 (3H, s). |
| A12 | 10.45 | 383.014 | 383.0131 | $C_{15}H_{12}Cl_2N_4O_2S$ | |
| A13 | 11.86 | 503.0685 | 503.0684 | $C_{23}H_{17}Cl_2FN_4O_4$ | (DMSO-d6) δ: 12.97 (1H, s), 9.09 (1H, s), 8.73 (1H, s) 7.39 (1H, d, J = 8.3 Hz), 7.26 (1H, dd, J = 8.3, 2.4 Hz), 6.95-6.88 (1H, m), 6.61-6.54 (2H, m), 6.10 (1H, d, J = 2.4 Hz), 5.59 (2H, s), 3.59 (3H, s), 2.43 (3H, s). |

TABLE 3-continued

| Compound Number | HPLC Retention Time | Obs. Mass [M + H]+ | Pred. Mass [M + H]+ | Formula (M) | $^1$H NMR |
|---|---|---|---|---|---|
| A14 | 10.85 | 435.1464 | 435.1463 | $C_{23}H_{19}FN_4O_4$ | (DMSO-d6) δ: 9.07 (1H, s), 8.71 (1H, s), 7.24-7.12 (4H, m), 6.88-6.82 (2H, m), 6.56-6.52 (2H, m), 5.71 (2H, s), 3.54 (3H, s), 2.40 (3H, s). |

Furthermore, in the Tables, the numeric values in the cells, which are noted as "[M−H]−," represent the values of [M−H]− observed by the above-mentioned instrument and analytical conditions.

Example 17

Test for Inhibition of Uric Acid Transport Using Human URAT1-Expressing Cells

A test compound was dissolved in DMSO (produced by Sigma) to a concentration of 20 mM and was subsequently used by adjusting the concentration to a desired value for use.

Full-length cDNA of human URAT1 (hURAT1) (produced by OriGene Technologies, Inc., NCBI Reference Sequence: NM-144585) was subcloned into an expression vector, pCMV6-Kan/Neo (produced by OriGene Technologies, Inc.), and human URAT1 genes were transfected into human embryonic kidney-derived cells (HEK 293 cells) by a liposome method using Lipofectamine 2000 (produced by Invitrogen Corporation), whereupon HEK 293 cells expressing human URAT1 genes were selected on the basis of Geneticin resistance. Functional expression of human URAT1 genes was confirmed by using transport of $^{14}$C-labeled uric acid into the cells as an index.

The HEK 293 cells expressing human URAT1 were seeded in a 24-well cell culture dish to a density of 3×10$^5$ cells/mL/well and were cultured in Dulbecco's modified Eagle's medium (D-MEM medium) containing 10% fetal bovine serum at 37° C. for 2 days. Thereafter, the following test for inhibition of uric acid transport was performed.

After the medium was removed by aspiration from each well, the cells were replaced with a solution obtained by substituting NaCl in Hanks' Balanced Salt Solution (HBSS) with Na gluconate (hereinafter, HBSS/Na-gluconate), and the cells were preincubated at 37° C. for about 10 minutes. After removing the HBSS/Na-gluconate by aspiration, a $^{14}$C-uric acid solution containing various concentrations of the Example compound listed in Table 4 and a radioactive ligand ($^{14}$C-labeled uric acid; final concentration 25 µM) was added, and an uptake reaction was carried out by incubating at 37° C. for 5 min. After the reaction, the $^{14}$C-labeled uric acid was removed by aspiration and the cells were washed three times with ice-cooled HBSS. The HEK 293 cells expressing human URAT1 were lysed in a 0.2 mol/L aqueous NaOH solution (hereafter, the cell sample) and sampled from the well. The cell sample and a liquid scintillation cocktail, ULTIMA GOLD (produced by PerkinElmer, Inc.) were mixed, and the radioactivity was measured by a liquid scintillation counter (manufactured by Beckman Coulter, Inc.).

The uric acid transport rate of the Example compound at each concentration (% of control uptake) was calculated relative to the radioactivity (radioactivity in human URAT1 expressing HEK 293 cells without addition of the Example compound (DMSO addition)) showing URAT1-specific uric acid transport as 100%, and the concentration (IC$_{50}$) of the Example compound at which the uric acid transport rate is inhibited by 50% was determined. The results are shown in the following table. In addition, the symbols (*, , and *) in the table represent the following inhibitory activity values:

IC$_{50}$≤0.2 µM: ***
0.2 µM<IC$_{50}$≤2 µM: **
2 µM<IC$_{50}$≤20 µM: *

TABLE 4

| Compound number | Inhibitory activity |
|---|---|
| A1 | *** |
| A2 | *** |
| A3 | *** |
| A4 | *** |
| A5 | *** |
| A6 | *** |
| A7 | *** |
| A8 | *** |
| A9 | *** |
| A10 | *** |
| A11 | *** |
| A12 | *** |
| A13 | ** |
| A14 | *** |
| A15 | *** |

Example 18

Testing Drug Efficacy in Cebus Apella

A test compound (3 mg/kg to 30 mg/kg) dispersed in a 0.5% methylcellulose solution was administered to cebus apella from the nasal cavity to the stomach using a disposable catheter and a syringe barrel. Blood samples were taken before administration and 30 minutes, 1 hour, 2 hours, 4 hours, 8 hours, 12 hours, and 24 hours after administration; and urine samples were collected for the time intervals of from immediately after to 4 hours after administration, from 4 hours to 8 hours after administration, from 8 hours to 16 hours after administration, and from 16 hours to 24 hours after administration. Concentrations of uric acid and creatinine in the blood and urine samples collected were measured by an automatic analyzer (JEOL Ltd.). Uric acid and creatinine were measured respectively using L-type Wako UA•F (Wako Pure Chemicals Industries, Ltd.) and L-type Creatinine F (Wako Pure Chemicals Industries, Ltd.). Uric acid clearance was calculated from the uric acid concentrations in blood and urine and, similarly, creatinine clearance was calculated from the creatinine concentrations. Based on these values, the uric acid excretion rate was determined according to the following equation:

Uric acid excretion rate (%)=(uric acid clearance/creatinine clearance)×100

In the present test, excellent activity of the compound A11 to promote uric acid excretion was confirmed.

From the above-mentioned results, it is shown that the pyrazine derivative of the present invention possesses excellent ability to promote uric acid excretion.

INDUSTRIAL APPLICABILITY

The pyrazine derivative or the pharmaceutically acceptable salt thereof, or the solvate thereof of the present invention is used as a pharmaceutical.

The invention claimed is:

1. A pyrazine derivative represented by the following formula (I) or a pharmaceutically acceptable salt thereof:

[Chemical formula 1]

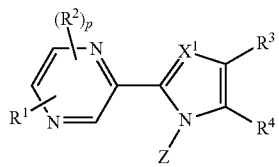

(I)

wherein, $X_1$ represents a nitrogen atom or CH;

$R^1$ represents a hydrogen atom, a $C_1$-$C_6$ alkyl group, a $C_3$-$C_6$ cycloalkyl group, a $C_2$-$C_6$ alkenyl group, a $C_2$-$C_6$ alkynyl group, a halogen atom, a trifluoromethyl group, a difluoromethyl group, a cyano group, a $C_2$-$C_7$ alkylcarbonyl group, a $C_1$-$C_6$ alkylsulfonyl group, a nitro group, an amino group, a di($C_1$-$C_6$ alkyl)amino group, a formyl group, a hydroxyl group, a $C_1$-$C_6$ alkoxy group, a $C_1$-$C_6$ alkylthio group, or a phenyl group or phenoxy group which may be substituted with 1 to 3 $R^a$'s;

$R^a$ represents a halogen atom, a $C_1$-$C_6$ alkyl group, a $C_3$-$C_6$ cycloalkyl group, or a $C_1$-$C_6$ alkoxy group;

$R^2$ represents a $C_1$-$C_6$ alkyl group, a $C_3$-$C_6$ cycloalkyl group, or a $C_1$-$C_6$ alkoxy group;

p represents any integer of 0 to 2;

$R^3$ represents a hydrogen atom, a $C_1$-$C_6$ alkyl group, a $C_3$-$C_6$ cycloalkyl group, a $C_2$-$C_6$ alkenyl group, a $C_2$-$C_6$ alkynyl group, a $C_1$-$C_6$ alkoxy group, a $C_2$-$C_7$ alkylcarbonyl group, a $C_1$-$C_6$ alkylthio group, a halogen atom, a trifluoromethyl group, a difluoromethyl group, a cyano group, a phenyl group, a pyridyl group, a phenoxy group, or a COOR$^b$;

$R^4$ represents a tetrazolyl group, —COOR$^c$, —CONHSO$_2$—($C_1$-$C_6$ alkyl), or any one of the following groups:

[Chemical formula 2]

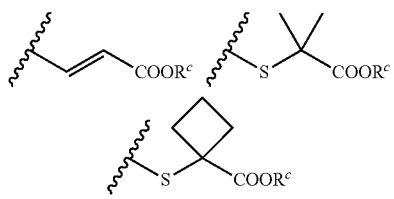

$R^b$ and $R^c$ may be the same or different and represent a hydrogen atom, or a $C_1$-$C_6$ alkyl group;

Z represents any one of the following groups represented by Z1 to Z7:

[Chemical formula 3]

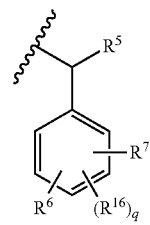 Z1

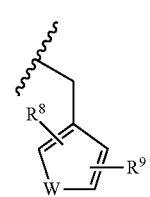 Z2

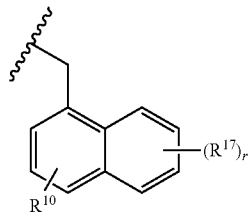 Z3

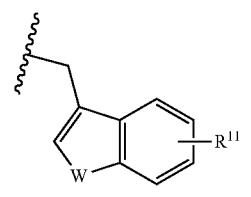 Z4

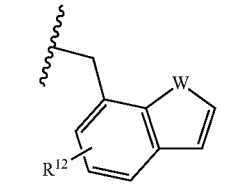 Z5

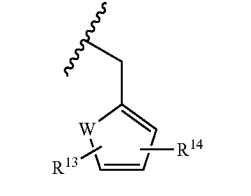 Z6

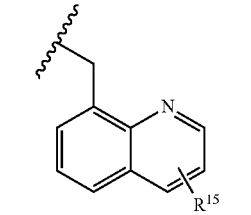 Z7

$R^5$ represents a hydrogen atom or a $C_1$-$C_6$ alkyl group;

$R^6$ and $R^7$ may be the same or different and represent a hydrogen atom, a halogen atom, a $C_1$-$C_6$ alkyl group, a $C_1$-$C_6$ alkoxy group, a trifluoromethyl group, a trifluoromethoxy group, a cyano group, a nitro group, or a phenoxy group, or $R^6$ and $R^7$ together form a $C_1$-$C_3$ alkylenedioxy group;

$R^8$, $R^9$, $R^{10}$, $R^{11}$, $R^{12}$, $R^{13}$, $R^{14}$, and $R^{15}$ each independently represent a hydrogen atom, a halogen atom, a $C_1$-$C_6$ alkyl group, a $C_1$-$C_6$ alkoxy group, a difluoromethyl group, a trifluoromethyl group, a cyano group, or a di($C_1$-$C_6$ alkyl)amino group;

$R^{16}$ and $R^{17}$ may be the same or different and represent a halogen atom;

q and r independently represent 0 or 1;

W represents a sulfur atom, an oxygen atom, or $NR^d$; and $R^d$ represents a hydrogen atom, a $C_1$-$C_6$ alkyl group, or a benzyl group.

2. The pyrazine derivative or the pharmaceutically acceptable salt thereof according to claim 1, wherein $X^1$ is a nitrogen atom.

3. The pyrazine derivative or the pharmaceutically acceptable salt thereof according to claim 1, wherein $X^1$ is CH.

4. The pyrazine derivative or the pharmaceutically acceptable salt thereof according to claim 1, wherein $R^1$ represents a hydrogen atom, a $C_1$-$C_6$ alkyl group, a $C_3$-$C_6$ cycloalkyl group, a halogen atom, a trifluoromethyl group, a cyano group, a hydroxyl group, a $C_1$-$C_6$ alkoxy group, a phenyl group, or a phenoxy group.

5. The pyrazine derivative or the pharmaceutically acceptable salt thereof according to claim 1, wherein $R^1$ represents a hydrogen atom, a methyl group, an ethyl group, a cyclopropyl group, an isopropyl group, a methoxy group, an ethoxy group, a cyano group, a hydroxyl group, a phenyl group, or a phenoxy group.

6. The pyrazine derivative represented by the following formula (1a) or the pharmaceutically acceptable salt thereof according to claim 1:

[Chemical formula 4]

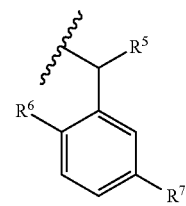

(Ia)

wherein $X^1$, $R^1$, $R^2$, $R^3$, $R^4$, p, and Z are the same as defined above.

7. The pyrazine derivative or the pharmaceutically acceptable salt thereof according to claim 1, wherein $R^3$ is a hydrogen atom, a $C_1$-$C_6$ alkyl group, or a halogen atom.

8. The pyrazine derivative or the pharmaceutically acceptable salt thereof according to claim 1, wherein $R^3$ is a hydrogen atom, a methyl group, or a chlorine atom.

9. The pyrazine derivative or the pharmaceutically acceptable salt thereof according to claim 1, wherein $R^4$ is —CO-$OR^c$.

10. The pyrazine derivative or the pharmaceutically acceptable salt thereof according to claim 1, wherein $R^4$ is a carboxyl group.

11. The pyrazine derivative or the pharmaceutically acceptable salt thereof according to claim 1, wherein Z represents Z1 or Z2, and W represents a sulfur atom.

12. The pyrazine derivative or the pharmaceutically acceptable salt thereof according to claim 1, wherein Z represents the following formula Z1a or Z2a:

[Chemical formula 5]

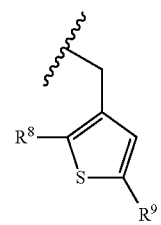

Z1a

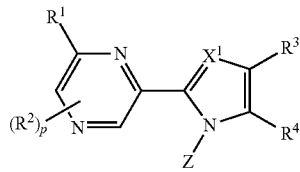

Z2a wherein, $R^5$, $R^6$, $R^7$, $R^8$, and $R^9$ are the same as defined above.

13. The pyrazine derivative or the pharmaceutically acceptable salt thereof according to claim 1, wherein $R^5$ represents a hydrogen atom; and $R^6$, $R^7$, $R^8$, and $R^9$ each independently represent a hydrogen atom, a halogen atom, or a $C_1$-$C_6$ alkyl group.

14. The pyrazine derivative or the pharmaceutically acceptable salt thereof according to claim 1, wherein p represents 0.

15. A pyrazine derivative selected from the following compounds (1) to (14) or a pharmaceutically acceptable salt thereof:

(1) 1-(2,5-dichlorobenzyl)-4-methyl-2-(pyrazin-2-yl)-1H-imidazole-5-carboxylic acid (2) 1-(2,5-dichlorobenzyl)-4-methyl-2-(6-methylpyrazin-2-yl)- 1H-imidazole-5-carboxylic acid (3) 1-(2,5-dichlorobenzyl)-2-(6-ethylpyrazin-2-yl)-4-methyl- 1H-imidazole-5-carboxylic acid (4) 1-(2,5-dichlorobenzyl)-4-methyl-2-(6-phenylpyrazin-2-yl)-1H-imidazole-5-carboxylic acid (5) 1-(2,5-dichlorobenzyl)-2-(6-methoxypyrazin-2-yl)-4-methyl-1H-imidazole-5-carboxylic acid (6) 1-(2,5-dichlorobenzyl)-4-methyl-2-(6-phenoxy-pyrazin-2-yl)-1H-imidazole-5-carboxylic acid (7) 1-(2,5-dichlorobenzyl)-2-(6-ethoxypyrazin-2-yl)-4-methyl-1H-imidazole-5-carboxylic acid (8) 2-(6-cyanopyrazin-2-yl)-1-(2,5-dichlorobenzyl)-4-methyl-1H-imidazole-5-carboxylic acid (9) 1-(2,5-dichlorobenzyl)-2-(6-isopropylpyrazin-2-yl)-4-methyl-1H-imidazole-5-carboxylic acid

(10) 2-(6-cyclopropylpyrazin-2-yl)-1-(2,5-dichlorobenzyl)-4-methyl-1H-imidazole-5-carboxylic acid

(11) 1-((2,5-dichlorothiophene-3-yl)methyl)-4-methyl-2-(pyrazin-2-yl)-1H-imidazole-5-carboxylic acid

(12) 1-((2,5-dichlorothiophene-3-yl)methyl)-4-methyl-2-(6-methylpyrazin-2-yl)-1H-imidazole-5-carboxylic acid

(13) 1-benzyl-2-(6-(2-fluoro-6-methoxyphenoxy)pyrazin-2-yl)-4-methyl-1H-imidazole-5-carboxylic acid

(14) 1-(2,5-dichlorobenzyl)-2-(pyrazin-2-yl)-1H-pyrrole-5-carboxylic acid.

16. A pharmaceutical composition containing the pyrazine derivative or the pharmaceutically acceptable salt thereof according to claim 1; and a pharmaceutically acceptable carrier.

17. A method of inhibiting URAT1 comprising administering an effective amount of the pyrazine derivative or the pharmaceutically acceptable salt thereof according to claim 1.

18. A method of treatment for one or more diseases selected from the group consisting of gout, hyperuricemia, hypertension, kidney diseases, diabetes, arteriosclerosis, or Lesch-Nyhan syndrome, comprising administering an effective amount of pyrazine derivative or the pharmaceutically acceptable salt thereof according to claim 1.

* * * * *